US011236322B2

(12) United States Patent
Corgie et al.

(10) Patent No.: US 11,236,322 B2
(45) Date of Patent: Feb. 1, 2022

(54) ENZYME FORMING MESOPOROUS ASSEMBLIES EMBEDDED IN MACROPOROUS SCAFFOLDS

(71) Applicant: CORNELL UNIVERSITY, Ithaca, NY (US)

(72) Inventors: Stephane C. Corgie, Ithaca, NY (US); Xiaonan Duan, Ithaca, NY (US); Emmanuel Giannelis, Ithaca, NY (US); Daniel Aneshansley, Ithaca, NY (US); Larry P. Walker, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/005,962

(22) Filed: Aug. 28, 2020

(65) Prior Publication Data
US 2021/0047630 A1    Feb. 18, 2021

Related U.S. Application Data

(60) Continuation of application No. 16/454,714, filed on Jun. 27, 2019, now Pat. No. 10,767,172, which is a
(Continued)

(51) Int. Cl.
| | | |
|---|---|---|
| C12N 9/02 | (2006.01) | |
| C12N 11/04 | (2006.01) | |
| A62D 3/02 | (2007.01) | |
| B01J 19/12 | (2006.01) | |
| B01J 35/04 | (2006.01) | |
| B01J 37/02 | (2006.01) | |
| C02F 1/48 | (2006.01) | |
| C02F 3/00 | (2006.01) | |
| C02F 3/34 | (2006.01) | |
| C07C 1/12 | (2006.01) | |
| C07G 1/00 | (2011.01) | |

(Continued)

(52) U.S. Cl.
CPC ............... *C12N 11/04* (2013.01); *A62D 3/02* (2013.01); *B01J 8/00* (2013.01); *B01J 19/12* (2013.01); *B01J 31/003* (2013.01); *B01J 31/02* (2013.01); *B01J 35/0033* (2013.01); *B01J 35/04* (2013.01); *B01J 37/02* (2013.01); *C02F 1/484* (2013.01); *C02F 3/00* (2013.01); *C02F 3/342* (2013.01); *C07C 1/12* (2013.01); *C07D 301/22* (2013.01); *C07G 1/00* (2013.01); *C08F 14/00* (2013.01); *C08F 18/00* (2013.01); *C12N 9/0004* (2013.01); *C12N 9/0006* (2013.01); *C12N 9/0061* (2013.01); *C12N 9/0065* (2013.01); *C12N 11/08* (2013.01); *C12N 11/14* (2013.01); *C12N 13/00* (2013.01); *C12P 7/04* (2013.01); *C12P 7/22* (2013.01); *C12P 17/02* (2013.01); *B01J 35/1061* (2013.01); *B01J 35/1066* (2013.01); *B01J 2208/00805* (2013.01); *B01J 2219/0854* (2013.01); *B01J 2219/0862* (2013.01); *C02F 2101/327* (2013.01); *C02F 2209/006* (2013.01); *C02F 2303/04* (2013.01); *C02F 2305/08* (2013.01); *C12Y 101/03004* (2013.01); *C12Y 111/01* (2013.01); *Y02P 20/50* (2015.11); *Y02W 10/40* (2015.05)

(58) Field of Classification Search
None
See application file for complete search history.

(56) References Cited

U.S. PATENT DOCUMENTS

| | | | |
|---|---|---|---|
| 4,152,210 A | 5/1979 | Robinson et al. | |
| 5,965,418 A | 10/1999 | Fuglsang et al. | |

(Continued)

FOREIGN PATENT DOCUMENTS

| | | | |
|---|---|---|---|
| CN | 1580233 A | 2/2005 | |
| CN | 101109016 A | 1/2008 | |

(Continued)

OTHER PUBLICATIONS

Salcedo, K. et al. Halogenation of Beta-Estradiol by a Rationally Designed Mesoporous Biocatalyst Based on Chloroperoxidase. Biocatalysis 1:33-43, 2015. (Year: 2015).*
Abdullah, M. et al., "Preparation of Oxide Particles with Ordered Macropores by Colloidal Templating and Spray Pyrolysis", Acta Materialia 52:5151-5156 (2004).
Azevedo, A.M. et al., "Horseradish Peroxidase: A Valuable Tool in Biotechnology", Biotechnology Annual Review, pp. 199-247 (2003).
Chalkias, N.G. et al., "Activity Increase of Horseradish Peroxidase in the Presence of Magnetic Particles", J. Am. Chem. Soc. 130:2910-2911 (2008).

(Continued)

*Primary Examiner* — Ralph J Gitomer
(74) *Attorney, Agent, or Firm* — Scully, Scott, Murphy & Presser, P.C.

(57) ABSTRACT

A hierarchical catalyst composition comprising a continuous or particulate macroporous scaffold in which is incorporated mesoporous aggregates of magnetic nanoparticles, wherein an enzyme is embedded in mesopores of the mesoporous aggregates of magnetic nanoparticles. Methods for synthesizing the hierarchical catalyst composition are also described. Also described are processes that use the recoverable hierarchical catalyst composition for depolymerizing lignin, remediation of water contaminated with aromatic substances, polymerizing monomers by a free-radical mechanism, epoxidation of alkenes, halogenation of phenols, inhibiting growth and function of microorganisms in a solution, and carbon dioxide conversion to methanol. Further described are methods for increasing the space time yield and/or total turnover number of a liquid-phase chemical reaction that includes magnetic particles to facilitate the chemical reaction, the method comprising subjecting the chemical reaction to a plurality of magnetic fields of selected magnetic strength, relative position in the chemical reaction, and relative motion.

8 Claims, 22 Drawing Sheets

Related U.S. Application Data division of application No. 15/701,920, filed on Sep. 12, 2017, now Pat. No. 10,351,841, which is a division of application No. 14/433,242, filed as application No. PCT/US2013/063441 on Oct. 4, 2013, now Pat. No. 9,765,324.

(60) Provisional application No. 61/710,110, filed on Oct. 5, 2012, provisional application No. 61/767,477, filed on Feb. 21, 2013.

(51) Int. Cl.

| | | |
|---|---|---|
| C08F 14/00 | (2006.01) | |
| C08F 18/00 | (2006.01) | |
| C07D 301/22 | (2006.01) | |
| C12N 11/14 | (2006.01) | |
| C12P 7/22 | (2006.01) | |
| C12N 9/04 | (2006.01) | |
| C12N 9/08 | (2006.01) | |
| C12N 13/00 | (2006.01) | |
| C12P 7/04 | (2006.01) | |
| C12P 17/02 | (2006.01) | |
| B01J 31/00 | (2006.01) | |
| B01J 35/00 | (2006.01) | |
| B01J 31/02 | (2006.01) | |
| B01J 8/00 | (2006.01) | |
| C12N 11/08 | (2020.01) | |
| B01J 35/10 | (2006.01) | |
| C02F 101/32 | (2006.01) | |

(56) References Cited

U.S. PATENT DOCUMENTS

| | | |
|---|---|---|
| 6,440,711 B1 | 8/2002 | Dave |
| 7,459,145 B2 | 12/2008 | Bao et al. |
| 7,485,367 B2 | 2/2009 | Chen et al. |
| 7,731,954 B2 | 6/2010 | Davis et al. |
| 9,597,672 B2 | 3/2017 | Corgie et al. |
| 9,765,324 B2 | 9/2017 | Corgie et al. |
| 10,260,061 B2 | 4/2019 | Corgie et al. |
| 10,316,313 B2 | 6/2019 | Corgie et al. |
| 10,351,841 B2 | 7/2019 | Corgie et al. |
| 2004/0166547 A1 | 8/2004 | Sullivan et al. |
| 2006/0289354 A1 | 12/2006 | Zhou et al. |
| 2008/0305048 A1 | 12/2008 | Josephson et al. |
| 2010/0056360 A1 | 3/2010 | Lee |
| 2010/0056816 A1 | 3/2010 | Wallin et al. |
| 2014/0004583 A1 | 1/2014 | Corgie et al. |
| 2015/0252352 A1 | 9/2015 | Corgie et al. |
| 2017/0096658 A1 | 4/2017 | Corgie et al. |
| 2017/0175101 A1 | 6/2017 | Corgie et al. |
| 2017/0189960 A1 | 7/2017 | Ibe |
| 2018/0087043 A1 | 3/2018 | Corgie et al. |
| 2018/0146663 A1 | 5/2018 | Corgie |
| 2018/0200701 A1 | 7/2018 | Corgie et al. |
| 2019/0174746 A1 | 6/2019 | Corgie et al. |
| 2019/0309282 A1 | 10/2019 | Corgie et al. |
| 2020/0002698 A1 | 1/2020 | Corgie et al. |
| 2020/0330967 A1* | 10/2020 | Corgie ............... B01J 35/0013 |

FOREIGN PATENT DOCUMENTS

| | | |
|---|---|---|
| CN | 101198255 A | 6/2008 |
| KR | 2011/033575 A | 3/2011 |
| SU | 1000098 | 2/1983 |
| WO | 8802600 A1 | 4/1988 |
| WO | WO 9111105 A1 | 8/1991 |
| WO | WO 9922597 A1 | 5/1999 |
| WO | WO 2006004557 A1 | 1/2006 |
| WO | WO 2012/122437 A2 | 9/2012 |
| WO | WO 2014055853 A1 | 4/2014 |
| WO | WO 2015/100432 A2 | 7/2015 |
| WO | WO 2017/180383 A1 | 10/2017 |
| WO | WO 2018/102319 A1 | 6/2018 |

OTHER PUBLICATIONS

Chinese Office Action dated Mar. 23, 2016 issued in corresponding Chinese Patent Application No. 201380063389.8 with English-language translation.

Corgie, S.C. et al., "Self-Assembled Complexes of Horseradish Peroxidase with Magnetic Nanoparticles Showing Enhanced Peroxidase Activity", Advanced Functional Materials 22:1940-1951 (Feb. 15, 2012).

Corgie, et al., "Self-Assemblies of Magnetic Nanoparticles (MNPs) and Peroxidase Enzymes: Mesoporous Structures and Nanoscale Magnetic Field Effects (nano-MFEs) for Enhanced Activity BioNanoCatalysts (BNCs)"; Cleantech, pp. 304-307, (2012).

Corvini, P.F.X. et al., "Lance: Laccase-Nanoparticle Conjugates for the Elimination of Micropollutants (Endocrine Disrupting Chemicals) from Wastewater in Bioreactors", Rev Environ Sci Biotechnol 9:23-27, (2010).

Davis, M. et al., "Formation of Three-Dimensional Ordered Hierarchically Porous Metal Oxides Vi Hybridized Epoxide Assisted/Colloidal Templating Approach", ACS Applied Materials & Interfaces 5:7786-7792 (2013).

El-Zahab, et al. "Enabling multienzyme biocatalysis using nanoporous materials," Biotechnol Bioeng, Jul. 20, 2004, vol. 87, No. 2, pp. 178-183.

Extended European Search Report dated Oct. 8, 2018 issued in EP Application No. 16796938.5.

Hielscher, Thomas. "Ultrasonic production of nano-size dispersions and emulsions," ENS 05, Paris, France, XP-002788816, Dec. 2005.

Huang, J. et al., "Zine Tetraaminophthalocynanine-Fe3O4 Nanoparticle Composite for Laccase Immobilization", International Journal of Nanomedicine 2(4): 775-784 (2007).

Hydrolase Nomenclature excerpt from Enzyme Nomenclature Recommendations Nomenclature Committee of the International Union of Biochemistry and Molecular Biology download from https://www.qmul.ac.uk/sbcs/iubmb/enzyme/EC3/ on Nov. 22, 2019.

International Search Report dated Oct. 10, 2012 received from the Korean Intellectual Property Office from Application No. PCT/US2012/028392.

International Search Report dated Feb. 20, 2014 received from Application No. PCT/US2013/063441.

International Search Report and Written Opinion dated Feb. 12, 2018 issued in PCT/US2017/063542.

International Search Report and Written Opinion dated Dec. 11, 2019 issued in PCT/US19/053307.

Kim, M. et al., Colorimetric Quantification of Galactose Using a Nanostructured Multicatalyst System. . . Analyst 137(5) 1137-1143, 2012.

Kim, J. et al., A Magnetically Separable Highly Stable Enzyme System Based on Nanocomposites of Enzymes. . . Small 1(12)1203-7, 2005.

Lee, J. et al., Magnetically Separable and Highly Stable Enzyme System Based on Crosslinked Enzyme Aggregates Shipped in Magnetite Coated Mesoporous Silica J of Materials Chemistry 19(42)864-70, 2009.

Lee, et al. "Microfluidic continuous magnetophoretic protein separation using nanoparticle aggregates," Microfluidic and Nanofluidic, Springer, Berlin, DE, vol. 11, No. 4, pp. 429-438, May 27, 2011.

Liu, et al. "Nanoparticle-supported multi-enzyme biocatalysis with in situ cofactor regeneration," J Biotechnol, Oct. 19, 2008, vol. 139, No. 1, pp. 102-107.

Lou, X-L et al., "Electronically Deposited Chitosan Hydrogel for Horseradish Peroxidase Immobilization Through Gold Nanoparticles Self-Assembly", Biosensors and Bioelectronics 21:190-196 (2005).

Morrison, M. et al., "Peroxidase-Catalyzed Halogenation", Annual Review of Biochemistry 45:861-888 (Jul. 1976), abstract.

Niu, T. et al., "Preparation of Meso-Macroporous alpha-Alumina Using Carbon Nanotube as the Template for the Mesopore and Their Application to the Preferential Oxidation of CO in H2-Rich Gases", J Porous Mater 20:789-798 (2013).

(56) References Cited

OTHER PUBLICATIONS

Pecova, M. et al. "Thermostable trypsin conjugates immobilized to biogenic magnetite show a high operational stability and remarkable reusability for protein digestion," Nanotechnology 2013 vol. 2013 125102 pp. 1-11.

Petkova, et al. "Synthesis of silica particles and their application as supports for alcohol dehydrogenases and cofactor immobilizations: conformational changes that lead to switch in enzyme stereoselectivity," Biochim Biophys Acta, Mar. 26, 2012, vol. 1824, No. 6, pp. 792-801.

Ping, Z. et al., "Research and application of magnetic fluidized bed", Chemical Industry and Engineering Progress, (Apr. 25, 2006), pp. 371-377, with English abstract.

Seelan, S. et al., "Macroporous Ceramics Coated With Mesoporous Layer for Enzyme Encapsulation", Key Engineering Materials 317-318: 717-722 (2006).

Supplementary European Search Report dated Sep. 29, 2016 issued in EP 13 84 4083.9.

Supplementary Partial European Search Report dated Apr. 29, 2016 issued in EP 13844083.9.

Tang, D. et al., "Direct Electrochemical Immunoassay Based on Immobilization of Protein-Magnetic Nanoparticle Composites on to Magnetic Electrode Surfaces by Sterically Enhanced Magnetic Field Force", Biotechnology Letters 28: 559-565 (2006).

Veitch, N.C., "Horseradish Peroxidase: A Modem View of a Classic Enzyme", Phytochemistry 65:249-259 (2004).

Wang, F. et al., "Magnetic Mesoprous Silica Nanoparticles: Fabrication and Their Laccase Immobilization Performance", Bioresource Technology 101:8931-8935 (2010).

Yang, H-H et al., "Magnetite-Containing Spherical Silica Nanoparticles for Biocatalysis and Bioseparations", Analytical Chemistry 76(5): 1316-1321 (Mar. 1, 2004).

Yang, L. et al., "Robust Macroporous Materials of Chiral Polyaniline Composites", Chem. Mater. 18(2): 297-300 (2006).

Zheng, et al. "Magnetic field intensified bi-enzyme system with in situ cofactor regeneration supported by magnetic nanoparticles," J Biotechnol, Jun. 10, 2013, vol. 168, No. 2, pp. 212-217.

\* cited by examiner (12A)

(12B)

ENZYME FORMING MESOPOROUS ASSEMBLIES EMBEDDED IN MACROPOROUS SCAFFOLDS

CROSS-REFERENCE TO RELATED APPLICATIONS

This application claims priority from U.S. Provisional Application No. 61/710,110, filed Oct. 5, 2012, and U.S. Provisional Application No. 61/767,477, filed Feb. 21, 2013, both of which are herein incorporated by reference in their entirety.

STATEMENT REGARDING FEDERALLY SPONSORED RESEARCH

This invention was made with government support under contract to the Northeast Sun Grant Initiative at Cornell University US Department of Transportation Assistance #DTOS59-07-G-00052. The government has certain rights in the invention.

BACKGROUND OF THE DISCLOSURE

Peroxidases (EC 1.11.1) are widely found in biological systems and form a subset of oxidoreductases that reduce hydrogen peroxide ($H_2O_2$) to water in order to oxidize a large variety of aromatic compounds ranging from phenol to aromatic amines. The reaction cycle of peroxidases is quite complex and begins with activation of heme by $H_2O_2$ to form the two-electron activated Compound I (N. C. Veitch, *Phytochemistry*, 2004, 65, 249). Compound I is then reduced by one electron by the oxidation of the organic substrate leading to the formation of Compound II that is one electron above the resting state. The second reduction recovers the enzyme to its resting state to start a new cycle. Overall, for each molecule of hydrogen peroxide consumed, two aromatic free radicals are produced and can readily react in secondary reactions.

Peroxidases are highly sensitive to substrate inhibition, mostly by $H_2O_2$, which can lead to the formation of the reversible inactivated form of the enzyme (Compound III). Their activities are also deterred by product inhibition. Therefore, the complex kinetics associated with peroxidase enzymes can restrict their use in many processes and bioprocesses. Increasing the activities of this and other families of enzymes and their tolerance to different process conditions could improve their current use, as well as pave the way for their use in new applications.

BRIEF SUMMARY OF THE DISCLOSURE

It has been discovered herein that bionanocatalysts (BNCs) consisting of an enzyme, particularly a free-radical-producing (FRP) enzyme, such as horseradish peroxidase (HRP), self-assembled with magnetic nanoparticles (MNPs) possess an enhanced enzymatic activity. In particular, it has herein been found that the self-assembled clusters of enzyme and magnetic nanoparticles generally possess faster turnover and lower inhibition of the enzyme as compared with the free enzyme or the magnetic nanoparticle clusters without enzyme. It has herein furthermore been found that the size and magnetization of the MNPs affect the formation and ultimately the structure of the BNCs, all of which have a significant impact on the activity of the entrapped enzymes. Particularly by virtue of their surprising resilience under various reaction conditions, the BNCs described herein can be used as an improved enzymatic or catalytic agent where other such agents are currently used, and they can furthermore be used in other applications where an enzyme has not yet been considered or found applicable.

The approach described herein sharply differs from classical methods that rely on protein conjugation on surface-modified particles by complex biochemistries, oftentimes at the expense of enzymatic activities and reaction efficiencies. By the instant methodology, enzyme kinetics are substantially modified only when the enzymes are in close association with the MNPs, e.g., as a self-assembled cluster (agglomeration) of primary MNP crystallites and peroxidase enzyme. The overall activities of the resulting BNCs can advantageously be orders of magnitude higher than those of free enzymes or MNPs at biologically relevant substrate concentration.

In one aspect, the invention is directed to a composition in which an enzyme is embedded (i.e., entrapped) in magnetic nanoparticles or clusters thereof. In particular embodiments, the composition is a mesoporous clustered assembly of magnetic nanoparticles and one or a combination of enzymes, such as FRP enzymes. The mesoporous clustered assemblies possess mesopores in which the enzyme is embedded. In other embodiments, the foregoing cluster composition includes magnetic nanoparticles that are surface-coated with a noble metal, such as gold.

In further embodiments, the foregoing mesoporous aggregates of magnetic nanoparticles (BNCs) are incorporated into a macroporous scaffold to form a hierarchical catalyst assembly with first and second levels of assembly. The macroporous scaffold may be constructed of an assemblage of micron-sized magnetic particles, or may be a continuous scaffold, which is not constructed from particles, or even a combination thereof. The result is a combination of highly macroporous and mesoporous magnetic solids with enzyme functionalization, which is beneficial to immobilization of any enzymes with small diffusible substrates and products. The overall hierarchical catalyst assembly is magnetic by at least the presence of the BNCs.

In the case of a continuous macroporous scaffold, in a first set of embodiments, the continuous macroporous scaffold in which the BNCs are incorporated is magnetic. The continuous macroporous scaffold can be magnetic by either being composed of a magnetic polymer composition and/or by having embedded therein magnetic particles not belonging to the BNCs (e.g., magnetic nano- or micro-particles not associated with the enzyme). In a second set of embodiments, the continuous scaffold in which the BNCs are incorporated is non-magnetic; nevertheless, the overall hierarchical catalyst assembly containing the non-magnetic scaffold remains magnetic by at least the presence of the BNCs incorporated therein.

The invention is also directed to a process for producing the enzyme-embedded magnetic nanoparticle compositions described above. In some embodiments, magnetic nanoparticles or aggregates thereof are first prepared, and the enzyme is subsequently absorbed therein. In other embodiments, the enzyme-embedded magnetic nanoparticle composition is produced by assembling monodispersed magnetic nanoparticles in the presence of an enzyme, thereby embedding the enzyme in clusters of MNPs by a self-assembly mechanism.

The invention is also directed to a process for producing the hierarchical catalyst assembly, described above, in which mesoporous aggregates of magnetic nanoparticles (BNCs) are incorporated into a continuous or particulate macroporous scaffold. In the method, BNCs are contacted with the macroporous scaffold in solution to substantially embed the BNCs into macropores of the macroporous scaffold. In the particular case of a continuous macroporous scaffold, the continuous macroporous scaffold can be produced by a templating process that includes: (i) producing a composite containing a scaffold precursor material having embedded therein a sacrificial templating agent, and (ii) selective removal of the sacrificial templating agent to produce macropores in the continuous precursor material. In more specific embodiments, the templating process involves a solvent templation process wherein a solvent, embedded in the scaffold precursor material, functions as a templating agent. The composite containing the scaffold precursor material embedded with solvent is cooled until the embedded solvent freezes to form solvent crystals, and then the frozen solvent is removed by either evaporation or sublimation to produce macropores in the scaffold precursor material. When the solvent is water, the solvent templating process can be considered an ice templation process.

In yet other aspects, the invention is directed to processes in which the above-described enzyme-embedded magnetic nanoparticle compositions are used. In particular embodiments, the enzyme-embedded magnetic nanoparticle compositions are directed to a process for depolymerizing lignin, a process for removing aromatic contaminants from water, a process for producing a polymer by polymerizing a monomer by a free radical mechanism, a method for epoxidation of alkenes, a method for halogenation of phenols, a method for inhibiting growth and function of microorganisms in a solution, and a method for carbon dioxide conversion to methanol.

In still other aspects, the invention is directed to a method for increasing a space time yield and/or total turnover number of a liquid-phase chemical reaction that includes magnetic particles, such as any of the BNCs or hierarchical catalyst assemblies thereof, to facilitate the chemical reaction. In the method, the liquid-phase chemical reaction containing magnetic particles therein is subjected to a plurality of magnetic fields of selected magnetic strength, relative position in the liquid-phase chemical reaction, and relative motion to spatially confine the magnetic particles, wherein the magnetic strength, relative positioning, and relative motion of the plurality of magnetic fields are provided by a system of electromagnets in which current flow is appropriately controlled or adjusted.

By virtue of the larger size and the mass magnetization of the overall hierarchical assembly containing BNCs incorporated into the macroporous framework, the enzyme-containing BNCs can be more easily captured by an external magnetic field, and thus, more easily removed from a reaction medium. The simplified removal furthermore permits the more facile re-use of the catalysts. Another benefit of the hierarchical assembled catalysts described herein is that the larger size helps to preserve enzymatic activities. Moreover, BNCs attached onto the surface of magnetic microparticles are less prone to over-aggregation when subjected to magnetic fields that may be used to remove the BNCs or enhance the reaction.

BRIEF DESCRIPTION OF THE FIGURES

FIG. 8A: Glucose oxidase was at 6.125 nM (4A: ratio of 4); FIG. 8B: 12.5 nM (4B: ratio of 2), and FIG. 8C: 25 nM (4C: ratio of 1). The BNCs can accommodate an in situ hydrogen production system to increase the release of aromatics from biomass and use glucose as oxidant.

FIG. 11A is for [MMP]/[MNP]/[HRP]=20:2:1, and FIG. 11B is for [MMP]/[MNP]/[HRP]=160:2:1. The error bars are the standard deviation of triplicates. The hierarchical structures allow the reuse of the enzyme catalysts for several cycles.

DETAILED DESCRIPTION OF THE DISCLOSURE

Figure 1A:
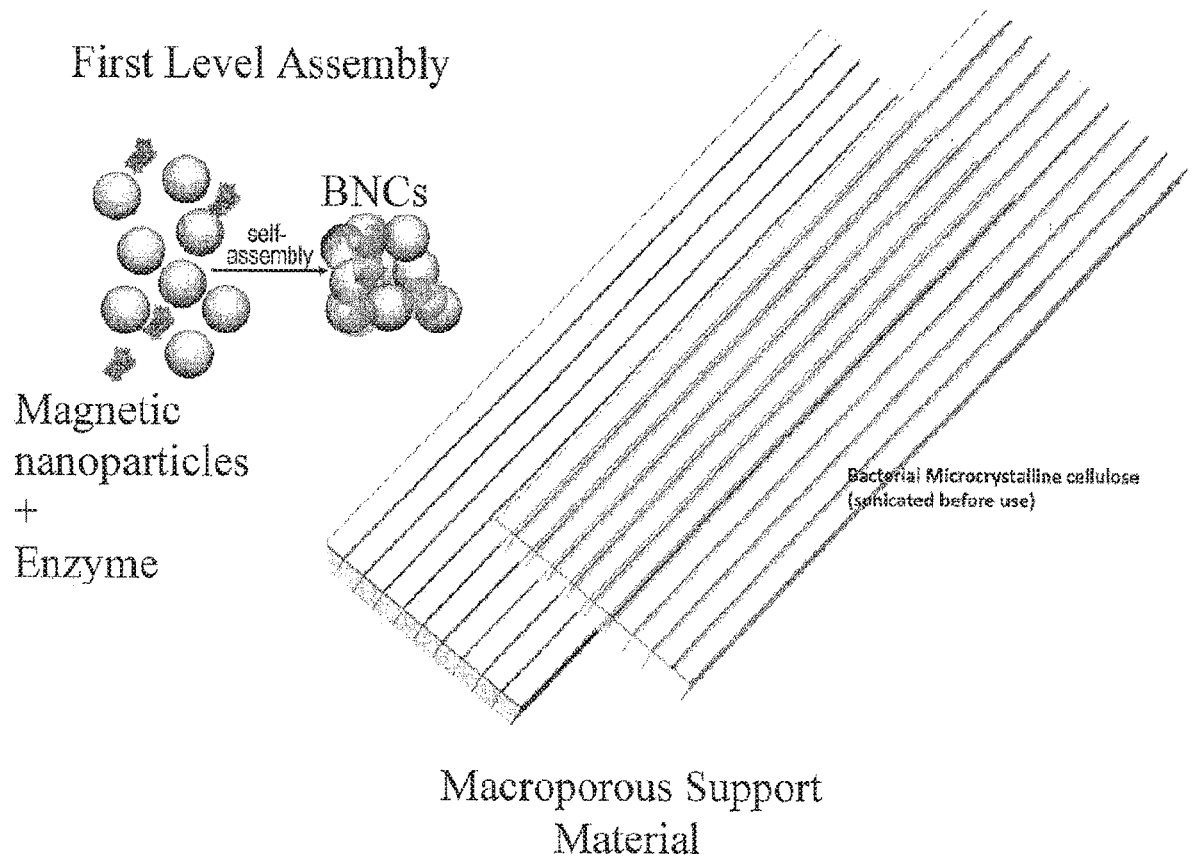
FIGS. 1A, 1B. Formation of the first level of assembly of a hierarchical catalyst assembly containing BNCs composed of mesoporous aggregates of magnetic nanoparticles and horseradish peroxidase (FIG. 1A), and formation of the second level of assembly by incorporating the BNCs into a macroporous scaffold composed of ice-templated cellulose (FIG. 1B).

In one aspect, the invention is directed to an enzyme-containing composition that includes mesoporous aggregates of magnetic nanoparticles adsorbed to one or more enzymes, wherein the one or more enzymes may or may not include a free-radical producing (FRP) enzyme. The assembly of magnetic nanoparticles adsorbed to enzyme is herein also referred to as a "bionanocatalyst" or "BNC". As used herein, the term "adsorbed" is meant to be synonymous with the terms "bound", "associated with", or "aggregated with", as long as the mode of attachment prevents or substantially minimizes release of the enzyme from the magnetic nanoparticles under conditions in which they are used or stored for later use. The BNCs or noble-metal coated versions thereof may also be adsorbed onto (i.e., be made to reside on) the surface of a macroporous scaffold, which may be an assembly of magnetic microparticles and/or any of the continuous macroporous scaffolds described below.

The BNC contains mesopores that are interstitial spaces between the magnetic nanoparticles. The enzyme may be located anywhere on the magnetic nanoparticle, e.g., on the surface and/or embedded within at least a portion of mesopores of the BNC. As used herein, the term "magnetic" encompasses all types of useful magnetic characteristics, including permanent magnetic, superparamagnetic, paramagnetic, ferromagnetic, and ferrimagnetic behaviors.

The magnetic nanoparticle or BNC has a size in the nanoscale, i.e., generally no more than 500 nm. As used herein, the term "size" can refer to a diameter of the magnetic nanoparticle when the magnetic nanoparticle is approximately or substantially spherical. In a case where the magnetic nanoparticle is not approximately or substantially spherical (e.g., substantially ovoid or irregular), the term "size" can refer to either the longest the dimension or an average of the three dimensions of the magnetic nanoparticle. The term "size" may also refer to an average of sizes over a population of magnetic nanoparticles (i.e., "average size"). In different embodiments, the magnetic nanoparticle has a size of precisely, about, up to, or less than, for example, 500 nm, 400 nm, 300 nm, 200 nm, 100 nm, 50 nm, 40 nm, 30 nm, 25 nm, 20 nm, 15 nm, 10 nm, 5 nm, 4 nm, 3 nm, 2 nm, or 1 nm, or a size within a range bounded by any two of the foregoing exemplary sizes.

In the BNC, the individual magnetic nanoparticles can be considered to be primary nanoparticles (i.e., primary crystallites) having any of the sizes provided above. The aggregates of nanoparticles in a BNC are larger in size than the nanoparticles and generally have a size (i.e., secondary size) of at least 5 nm. In different embodiments, the aggregates have a size of precisely, about, at least, above, up to, or less than, for example, 5 nm, 8 nm, 10 nm, 12 nm, 15 nm, 20 nm, 25 nm, 30 nm, 35 nm, 40 nm, 45 nm, 50 nm, 60 nm, 70 nm, 80 nm, 90 nm, 100 nm, 150 nm, 200 nm, 300 nm, 400 nm, 500 nm, 600 nm, 700 nm, or 800 nm, or a size within a range bounded by any two of the foregoing exemplary sizes.

Typically, the primary and/or aggregated magnetic nanoparticles or BNCs thereof have a distribution of sizes, i.e., they are generally dispersed in size, either narrowly or broadly dispersed. In different embodiments, any range of primary or aggregate sizes can constitute a major or minor proportion of the total range of primary or aggregate sizes. For example, in some embodiments, a particular range of primary particle sizes (for example, at least 1, 2, 3, 5, or 10 nm and up to 15, 20, 25, 30, 35, 40, 45, or 50 nm) or a particular range of aggregate particle sizes (for example, at least 5, 10, 15, or 20 nm and up to 50, 100, 150, 200, 250, or 300 nm) constitutes at least or above 50%, 60%, 70%, 80%, 90%, 95%, 98%, 99%, or 100% of the total range of primary particle sizes. In other embodiments, a particular range of primary particle sizes (for example, less than 1, 2, 3, 5, or 10 nm, or above 15, 20, 25, 30, 35, 40, 45, or 50 nm) or a particular range of aggregate particle sizes (for example, less than 20, 10, or 5 nm, or above 25, 50, 100, 150, 200, 250, or 300 nm) constitutes no more than or less than 50%, 40%, 30%, 20%, 10%, 5%, 2%, 1%, 0.5%, or 0.1% of the total range of primary particle sizes.

The aggregates of magnetic nanoparticles (i.e., "aggregates") or BNCs thereof can have any degree of porosity, including a substantial lack of porosity depending upon the quantity of individual primary crystallites they are made of. In particular embodiments, the aggregates are mesoporous by containing interstitial mesopores (i.e., mesopores located between primary magnetic nanoparticles, formed by packing arrangements). The mesopores are generally at least 2 nm and up to 50 nm in size. In different embodiments, the mesopores can have a pore size of precisely or about, for example, 2, 3, 4, 5, 10, 12, 15, 20, 25, 30, 35, 40, 45, or 50 nm, or a pore size within a range bounded by any two of the foregoing exemplary pore sizes. Similar to the case of particle sizes, the mesopores typically have a distribution of sizes, i.e., they are generally dispersed in size, either narrowly or broadly dispersed. In different embodiments, any range of mesopore sizes can constitute a major or minor proportion of the total range of mesopore sizes or of the total pore volume. For example, in some embodiments, a particular range of mesopore sizes (for example, at least 2, 3, or 5, and up to 8, 10, 15, 20, 25, or 30 nm) constitutes at least or above 50%, 60%, 70%, 80%, 90%, 95%, 98%, 99%, or 100% of the total range of mesopore sizes or of the total pore volume. In other embodiments, a particular range of mesopore sizes (for example, less than 2, 3, 4, or 5 nm, or above 10, 15, 20, 25, 30, 35, 40, 45, or 50 nm) constitutes no more than or less than 50%, 40%, 30%, 20%, 10%, 5%, 2%, 1%, 0.5%, or 0.1% of the total range of mesopore sizes or of the total pore volume.

The magnetic nanoparticles can have any of the compositions known in the art. In some embodiments, the magnetic nanoparticles are or include a zerovalent metallic portion that is magnetic. Some examples of such zerovalent metals include cobalt, nickel, and iron, and their mixtures and alloys. In other embodiments, the magnetic nanoparticles are or include an oxide of a magnetic metal, such as an oxide of cobalt, nickel, or iron, or a mixture thereof. In some embodiments, the magnetic nanoparticles possess distinct core and surface portions. For example, the magnetic nanoparticles may have a core portion composed of elemental iron, cobalt, or nickel and a surface portion composed of a passivating layer, such as a metal oxide or a noble metal coating, such as a layer of gold, platinum, palladium, or silver. In other embodiments, metal oxide magnetic nanoparticles or aggregates thereof are coated with a layer of a noble metal coating. The noble metal coating may, for example, reduce the number of charges on the magnetic nanoparticle surface, which may beneficially increase dispersibility in solution and better control the size of the BNCs. The noble metal coating protects the magnetic nanoparticles against oxidation, solubilization by leaching or by chelation when chelating organic acids, such as citrate, malonate, or tartrate, are used in the biochemical reactions or processes. The passivating layer can have any suitable thickness, and particularly, at least, up to, or less than, for example, 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, or 10 nm, or a thickness in a range bounded by any two of these values.

In particular embodiments, the magnetic nanoparticles have an iron oxide composition. The iron oxide composition can be any of the magnetic or superparamagnetic iron oxide compositions known in the art, e.g., magnetite ($Fe_3O_4$), hematite ($\alpha$-$Fe_2O_3$), maghemite ($\gamma$-$Fe_2O_3$), or a spinel ferrite according to the formula $AB_2O_4$, wherein A is a divalent metal (e.g., $Zn^{2+}$, $Ni^{2+}$, $Mn^{2+}$, $Co^{2+}$, $Ba^{2+}$, $Sr^{2+}$, or combination thereof) and B is a trivalent metal (e.g., $Fe^{3+}$, $Cr^{3+}$, or combination thereof).

In particular embodiments, the above mesoporous aggregates of magnetic nanoparticles (BNCs) are incorporated into a continuous macroporous scaffold to form a hierarchical catalyst assembly with first and second levels of assembly. The first level of assembly is found in the BNCs. The second level of assembly is found in the incorporation of the BNCs into the continuous macroporous scaffold. The overall hierarchical catalyst assembly is magnetic by at least the presence of the BNCs.

The term "continuous", as used herein for the macroporous scaffold, indicates a material that is not a particulate assembly, i.e., is not constructed of particles or discrete objects assembled with each other to form a macroscopic structure. In contrast to a particulate assembly, the continuous structure is substantially seamless and uniform around macropores that periodically interrupt the seamless and uniform structure. The macropores in the continuous scaffold are, thus, not interstitial spaces between agglomerated particles. Nevertheless, the continuous scaffold can be constructed of an assembly or aggregation of smaller primary continuous scaffolds, as long as the assembly or aggregation of primary continuous scaffolds does not include macropores (e.g., from above 50 nm and up to 100 microns) formed by interstitial spaces between primary continuous scaffolds. Particularly in the case of inorganic materials, such as ceramics or elemental materials, the continuous scaffold may or may not also include crystalline domains or phase boundaries.

The macroporous scaffold contains macropores (i.e., pores of a macroscale size) having a size greater than 50 nm. In different embodiments, the macropores have a size of precisely, about, at least, above, up to, or less than, for example, 60 nm, 70 nm, 80 nm, 90 nm, 100 nm, 150 nm, 200 nm, 300 nm, 400 nm, 500 nm, 600 nm, 700 nm, 800 nm, 900 nm, 1 micron (1 µm), 1.2 µm, 1.5 µm, 2 µm, 3 µm, 4 µm, 5 µm, 10 µm, 20 µm, 30 µm, 40 µm, 50 µm, 60 µm, 70 µm, 80 µm, 90 µm, or 100 µm, or a size within a range bounded by any two of the foregoing exemplary sizes.

The macroporous scaffold can have any suitable size as long as it can accommodate macropores. In typical embodiments, the macroporous scaffold possesses at least one size dimension in the macroscale. The at least one macroscale dimension is above 50 nm, and can be any of the values provided above for the macropores, and in particular, a dimension of precisely, about, at least, above, up to, or less than, for example, 1 µm, 2 µm, 3 µm, 4 µm, 5 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 5 mm, or 1 cm, or a size within a range hounded by any two of the foregoing exemplary sizes. Where only one or two of the size dimensions are in the macroscale, the remaining one or two dimensions can be in the nanoscale, such as any of the values provided above for the magnetic nanoparticles (e.g., independently, precisely, about, at least, above, up to, or less than, for example, 1, 2, 3, 4, 5, 10, 20, 30, 40, 50, 60, 70, 80, 90, or 100 nm, or a value within a range bounded by any two of the foregoing values). In some embodiments, at least two or all of the size dimensions of the macroporous scaffold is in the macroscale.

In a first set of embodiments, the continuous macroporous scaffold in which the BNCs are incorporated is magnetic, i.e., even in the absence of the BNCs. The continuous macroporous scaffold can be magnetic by, for example, being composed of a magnetic polymer composition. An example of a magnetic polymer is PANiCNQ, which is a combination of tetracyanoquinodimethane (TCNQ) and the emeraldine-based form of polyaniline (PANi), as well known in the art. Alternatively, or in addition, the continuous macroporous scaffold can be magnetic by having embedded therein magnetic particles not belonging to the BNCs. The magnetic particles not belonging to the BNCs may be, for example, magnetic nano- or micro-particles not associated with an FRP enzyme or any enzyme. The magnetic microparticles may have a size or size distribution as provided above for the macropores, although independent of the macropore sizes. In particular embodiments, the magnetic microparticles have a size of about, precisely, or at least 20, 30, 40, 50, 60, 70, 80, 90, 100, 100, 200, 300, 400, 500, 600, 700, 800, 900, 1000 nm, or a size within a range bounded by any two of the foregoing exemplary sizes. In some embodiments, the continuous macroporous scaffold has embedded therein magnetic microparticles that are adsorbed to at least a portion of the BNCs, or wherein the magnetic microparticles are not associated with or adsorbed to the BNCs.

In a second set of embodiments, the continuous scaffold in which the BNCs are incorporated is non-magnetic. Nevertheless, the overall hierarchical catalyst assembly containing the non-magnetic scaffold remains magnetic by at least the presence of the BNCs incorporated therein.

In one embodiment, the continuous macroporous scaffold (or precursor thereof) has a polymeric composition. The polymeric composition can be any of the solid organic, inorganic, or hybrid organic-inorganic polymer compositions known in the art, and may be synthetic or a biopolymer that acts as a binder. Preferably, the polymeric macroporous scaffold does not dissolve or degrade in water or other medium in which the hierarchical catalyst is intended to be used. Some examples of synthetic organic polymers include the vinyl addition polymers (e.g., polyethylene, polypropylene, polystyrene, polyacrylic acid or polyacrylate salt, polymethacrylic acid or polymethacrylate salt, poly(methylmethacrylate), polyvinyl acetate, polyvinyl alcohol, and the like), fluoropolymers (e.g., polyvinylfluoride, polyvinylidenefluoride, polytetrafluoroethylene, and the like), the epoxides (e.g., phenolic resins, resorcinol-formaldehyde resins), the polyamides, the polyurethanes, the polyesters, the polyimides, the polybenzimidazoles, and copolymers thereof. Some examples of biopolymers include the polysaccharides (e.g., cellulose, hemicellulose, xylan, chitosan, inulin, dextran, agarose, and alginic acid), polylactic acid, and polyglycolic acid. In the particular case of cellulose, the cellulose may be microbial- or algae-derived cellulose. Some examples of inorganic or hybrid organic-inorganic polymers include the polysiloxanes (e.g., as prepared by sol gel synthesis, such as polydimethylsiloxane) and polyphosphazenes. In some embodiments, any one or more classes or specific types of polymer compositions provided above are excluded as macroporous scaffolds.

In another embodiment, the continuous macroporous scaffold (or precursor thereof) has a non-polymeric composition. The non-polymeric composition can have, for example, a ceramic or elemental composition. The ceramic composition may be crystalline, polycrystalline, or amorphous, and may have any of the compositions known in the art, including oxide compositions (e.g., alumina, beryllia, ceria, yttria, or zirconia) and non-oxide compositions (e.g., carbide, silicide, nitride, boride, or sulfide compositions). The elemental composition may also be crystalline, polycrystalline, or amorphous, and may have any suitable elemental composition, such as carbon, aluminum, or silicon.

In other embodiments, the BNCs reside in a non-continuous macroporous support containing (or constructed of) an assembly (i.e., aggregation) of magnetic microparticles (MMPs) that includes macropores as interstitial spaces between the magnetic microparticles. The magnetic microparticles are typically ferromagnetic. The BNCs are embedded in at least a portion of the macropores of the aggregation of magnetic microparticles, and may also reside on the surface of the magnetic microparticles. The BNCs can associate with the surface of the magnetic microparticles by magnetic interaction. The magnetic microparticles may or may not be coated with a metal oxide or noble metal coating layer. In some embodiments, the BNC-MMP assembly is incorporated (i.e., embedded) into a continuous macroporous scaffold, as described above, to provide a hierarchical catalyst assembly.

The individual magnetic nanoparticles or aggregates thereof or BNCs thereof possess any suitable degree of magnetism. For example, the magnetic nanoparticles, BNCs, or BNC-scaffold assemblies can possess a saturated magnetization ($M_s$) of at least or up to 5, 10, 15, 20, 25, 30, 40, 45, 50, 60, 70, 80, 90, or 100 emu/g. The magnetic nanoparticles, BNCs, or BNC-scaffold assemblies preferably possess a remnant magnetization ($M_r$) of no more than (i.e., up to) or less than 5 emu/g, and more preferably, up to or less than 4 emu/g, 3 emu/g, 2 emu/g, 1 emu/g, 0.5 emu/g, or 0.1 emu/g. The surface magnetic field of the magnetic nanoparticles, BNCs, or BNC-scaffold assemblies can be about or at least, for example, 0.5, 1, 5, 10, 50, 100, 200, 300, 400, 500, 600, 700, 800, 900, or 1000 Gauss (G), or a magnetic field within a range bounded by any two of the foregoing values. If microparticles are included, the microparticles may also possess any of the above magnetic strengths.

The magnetic nanoparticles or aggregates thereof can be made to adsorb a suitable amount of enzyme, up to or below a saturation level, depending on the application, to produce the resulting BNC. In different embodiments, the magnetic nanoparticles or aggregates thereof may adsorb about, at least, up to, or less than, for example, 1, 5, 10, 15, 20, 25, or 30 pmol/m$^2$ of enzyme. Alternatively, the magnetic nanoparticles or aggregates thereof may adsorb an amount of enzyme that is about, at least, up to, or less than, for example, 10%, 20%, 30%, 40%, 50%, 60%, 70%, 80%, 90%, or 100% of a saturation level.

The magnetic nanoparticles or aggregates thereof or BNCs thereof possess any suitable pore volume. For example, the magnetic nanoparticles or aggregates thereof can possess a pore volume of about, at least, up to, or less than, for example, 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm$^3$/g, or a pore volume within a range bounded by any two of the foregoing values.

The magnetic nanoparticles or aggregates thereof or BNCs thereof possess any suitable specific surface area. For example, the magnetic nanoparticles or aggregates thereof can have a specific surface area of about, at least, up to, or less than, for example, 50, 60, 70, 80, 90, 100, 110, 120, 130, 140, 150, 160, 170, 180, 190, or 200 m$^2$/g.

For purposes of the invention, the enzyme preferably functions by converting a diffusible substrate into a diffusible product. The enzyme can be from any source, e.g., fungal, microbial, animal, or plant.

In particular embodiments, the enzyme has the property of producing free radicals, i.e., is a "FRP enzyme". In particular embodiments, the FRP enzyme is an oxidoreductase belonging to the EC 1 family of enzymes. The EC 1 oxidoreductase can be, for example, an EC 1.1 oxidoreductase acting on the CH—OH groups of donors, an EC 1.2 oxidoreductase acting on the aldehyde or oxo group of donors, an EC 1.3 oxidoreductase acting on the CH—CH group of donors, an EC 1.4 oxidoreductase acting on the CH—NH$_2$ group of donors, an EC 1.5 oxidoreductase acting on the CH—NH group of donors, an EC 1.6 oxidoreductase acting on NADH or NADPH, an EC 1.7 oxidoreductase acting on various nitrogenous compounds as donors, an EC 1.8 oxidoreductase acting on a sulfur group as donor, an EC 1.9 oxidoreductase acting on a heme group of donors, an EC 1.10 oxidoreductase acting on diphenols and related substances as donors, an EC 1.11 oxidoreductase acting on peroxide as an acceptor, an EC 1.12 oxidoreductase acting on hydrogen as a donor, an EC 1.13 oxidoreductase acting on single donors with incorporation of molecular oxygen (oxygenases), an EC 1.14 oxidoreductase acting on paired donors with incorporation or reduction of molecular oxygen, an EC 1.15 oxidoreductase acting on superoxide as an acceptor, an EC 1.16 oxidoreductase that oxidize metal ions, an EC 1.17 oxidoreductase acting on CH or $CH_2$ groups, an EC 1.18 oxidoreductase acting on iron-sulfur proteins as a donor, an EC 1.19 oxidoreductase acting on reduced flavodoxin as a donor, an EC 1.20 oxidoreductase acting on phosphorus or arsenic as a donor, an EC 1.21 oxidoreductase acting on X—H and Y—H to form an X—Y bond, an EC 1.97 oxidoreductase, an EC 1.98 oxidoreductase that uses hydrogen as a reductant, and an EC 1.99 oxidoreductase that uses oxygen as an oxidant. The oxidoreductase may also be more particularly identified as belonging to a sub-genus of any of the EC 1.1 groupings provided above.

In a first particular set of embodiments, the FRP enzyme is selected from the EC 1.1 genus of oxidoreductase enzymes. The EC 1.1 enzyme can further be identified as belonging to any of the following sub-genuses: EC 1.1.1 with NAD or NADP as acceptor, EC 1.1.2 with a cytochrome as acceptor, EC 1.1.3 with oxygen as acceptor, EC 1.1.4 with disulfide as acceptor, EC 1.1.5 with quinone or similar compound as acceptor, and EC 1.1.99 with other acceptors. In more particular embodiments, the FRP enzyme is identified as belonging to a sub-genus of any of the EC 1.1 sub-genuses provided above. For example, the FRP enzyme can be identified as belonging to any of the sub-genuses of EC 1.1.3, such as EC 1.1.3.3 (malate oxidase), EC 1.1.3.4 (glucose oxidase), EC 1.1.3.5 (hexose oxidase), EC 1.1.3.6 (cholesterol oxidase), EC 1.1.3.7 (aryl-alcohol oxidase), EC 1.1.3.8 (L-gulonolactone oxidase), EC 1.1.3.9 (galactose oxidase), EC 1.1.3.10 (pyranose oxidase), EC 1.1.3.11 (L-sorbose oxidase), EC 1.1.3.12 (pyridoxine 4-oxidase), EC 1.1.3.13 (alcohol oxidase), EC 1.1.3.14 (catechol oxidase), EC 1.1.3.15 (2-hydroxy acid oxidase), EC 1.1.3.16 (ecdysone oxidase), EC 1.1.3.17 (choline oxidase), EC 1.1.3.18 (secondary-alcohol oxidase), EC 1.1.3.19 (4-hydroxymandelate oxidase), EC 1.1.3.20 (long-chain alcohol oxidase), EC 1.1.3.21 (glycerol-3-phosphate oxidase), EC 1.1.3.22, EC 1.1.3.23 (thiamine oxidase), EC 1.1.3.24 (L-galactonolactone oxidase), EC 1.1.3.25, EC 1.1.3.26, EC 1.1.3.27 (hydroxyphytanate oxidase), EC 1.1.3.28 (nucleoside oxidase), EC 1.1.3.29 (N-acylhexosamine oxidase), EC 1.1.3.30 (polyvinyl alcohol oxidase), EC 1.1.3.31, EC 1.1.3.32, EC 1.1.3.33, EC 1.1.3.34, EC 1.1.3.35, EC 1.1.3.36, EC 1.1.3.37 D-arabinono-1,4-lactone oxidase), EC 1.1.3.38 (vanillyl alcohol oxidase), EC 1.1.3.39 (nucleoside oxidase, $H_2O_2$ forming), EC 1.1.3.40 (D-mannitol oxidase), and EC 1.1.3.41 (xylitol oxidase).

In a second particular set of embodiments, the FRP enzyme is selected from the EC 1.10 genus of oxidoreductase enzymes. The EC 1.10 enzyme can further be identified as belonging to any of the following sub-genuses: EC 1.10.1 with NAD or NADP as acceptor EC 1.10.2 with cytochrome as acceptor, EC 1.10.3 with oxygen as acceptor, and EC 1.10.99 with other acceptors. The EC 1.10.1 enzyme can be more specifically, for example, EC 1.10.1.1, i.e., trans-acenaphthene-1,2-diol dehydrogenase. The EC 1.10.2 enzyme can be more specifically, for example, EC 1.10.2.1 (cytochrome-b5 reductase) or EC 1.10.2.2 (cytochrome-c reductase). The EC 1.10.3 enzyme can be more specifically, for example, EC 1.10.3.1 (catechol oxidase), EC 1.10.3.2 (laccase), EC 1.10.3.3 (L-ascorbate oxidase), EC 1.10.3.4 (o-aminophenol oxidase), EC 1.10.3.5 (3-hydroxyanthranilate oxidase), EC 1.10.3.6 (rifamycin-B oxidase), EC 1.10.3.7, or EC 1.10.3.8. The EC 1.10.99 enzyme can be more specifically, for example, EC 1.10.99.1 (plastoquinol-plastocyanin reductase), EC 1.10.99.2 (ribosyldihydronicotinamide dehydrogenase, quinone), or EC 1.10.99.3 (violaxanthin de-epoxidase).

In a third particular set of embodiments, the FRP enzyme is selected from the EC 1.11 genus of oxidoreductase enzymes. The EC 1.11 enzyme can further be identified as belonging to the sub-genus EC 1.11.1 (peroxidases). The EC 1.11.1 enzyme can be more specifically, for example, EC 1.11.1.1 (NADH peroxidase), EC 1.11.1.2 (NADPH peroxidase), EC 1.11.1.3 (fatty acid peroxidase), EC 1.11.1.4, EC 1.11.1.5 (cytochrome-c peroxidase), EC 1.11.1.6 (catalase), EC 1.11.1.7 (peroxidase), EC 1.11.1.8 (iodide peroxidase), EC 1.11.1.9 (glutathione peroxidase), EC 1.11.1.10 (chloride peroxidase), EC 1.11.1.11 (L-ascorbate peroxidase), EC 1.11.1.12 (phospholipid-hydroperoxide glutathione peroxidase), EC 1.11.1.13 (manganese peroxidase), EC 1.11.1.14 (diarylpropane peroxidase), or EC 1.11.1.15 (peroxiredoxin).

In particular embodiments, the FRP enzyme is a peroxidase. The peroxidase may also be further specified by function, e.g., a lignin peroxidase, manganese peroxidase, or versatile peroxidase. The peroxidase may also be specified as a fungal, microbial, animal, or plant peroxidase. The peroxidase may also be specified as a class I, class II, or class III peroxidase. The peroxidase may also be specified as a myeloperoxidase (MPO), eosinophil peroxidase (EPO), lactoperoxidase (LPO), thyroid peroxidase (TPO), prostaglandin H synthase (PGHS), glutathione peroxidase, haloperoxidase, catalase, cytochrome c peroxidase, horseradish peroxidase, peanut peroxidase, soybean peroxidase, turnip peroxidase, tobacco peroxidase, tomato peroxidase, barley peroxidase, or peroxidasin. In particular embodiments, the peroxidase is horseradish peroxidase.

In some embodiments, a single enzyme is used, which may or may not be a FRP enzyme. In other embodiments, a combination of enzymes is used, which may or may not include a FRP enzyme. The combination of enzymes can be, for example, any two or three oxidoreductase enzymes selected from any of the above classes or sub-classes therein. In some embodiments, a combination of FRP enzymes (e.g., EC 1 enzymes) is used. In particular embodiments, a combination of EC 1.1 enzymes is used. In other particular embodiments, a combination of EC 1.10 enzymes is used. In other particular embodiments, a combination of EC 1.11 enzymes is used. In other embodiments, a combination of any of the particular FRP enzymes described above and a peroxidase is used (e.g., a combination of a EC 1.1 or EC 1.1.3 enzyme and a peroxidase). When a combination of FRP enzymes is used, the two or more enzymes may be arranged in a core-shell type of arrangement, i.e., a first FRP enzyme is either in a core portion or surface portion of the magnetic nanoparticle or aggregate thereof, and a second (different) FRP enzyme covers the region where the first FRP enzyme is located. The second FRP enzyme may be an aggregate of the magnetic nanoparticle or on the surface thereof, overlaying the first enzyme.

In the case of multiple enzyme systems, manipulating the distribution of the different enzymes within the mesoporous aggregates offers the advantage of decoupling the different reactions and permitting diffusion of the substrates and products of the reactions from one layer to another layer or to the core of the BNCs. Therefore, when performing the enzymatic reactions in the confined pore structures of the BNCs, core/shell distributions offer the possibility of better controlling the kinetics of the different entrapped FRP enzymes. Combining enzymes that perform similar reactions (such as two, or more, peroxidases or a peroxidase and a laccase for example) but having different reaction requirements (substrates, substrate concentration, etc.) can beneficially increase the versatility of the BNCs to perform in broad and variable process conditions at a high level of efficiency. Combining enzymes with coupled reactions can ensure the production of the substrate in the vicinity of the enzyme and bypass the need for hazardous and labile chemical substrates, such as hydrogen peroxide. For example, a glucose oxidase enzyme can generate hydrogen peroxide from glucose, which is an inexpensive and non-hazardous compound.

In another aspect, the invention is directed to methods for producing the mesoporous aggregates of magnetic nanoparticles with enzyme embedded therein (BNCs). In particular embodiments, the BNCs are prepared by combining soluble enzymes with a monodispersed solution of magnetic nanoparticles, which may or may not be coated. The monodispersed state of the nanoparticle prior to mixing can be achieved by sonication of the nanoparticles. Enzymes and monodispersed nanoparticles are incubated under permanent agitation until all enzymes are adsorbed and clusters form. The pH of the solution for BNC synthesis needs to be such that the overall electrostatic charge of surface groups the enzymes is opposite to the overall electrostatic charge of the surface of the nanoparticles. For optimal formation of BNCs, the pH of the solution should be adjusted to prevent self-aggregation of the nanoparticles, and the presence of counterions is generally undesirable. In one embodiment, for optimal formation of BNCs, the surface potential of the enzymes (pKa) and the nanoparticles is no more than three units to limit over-aggregation and clumping. In another embodiment, for optimal formation of BNCs, the concentration of enzymes is no more than about 80% of the total binding capacity of the nanoparticle surface in order to prevent over-aggregation. The size of the BNC clusters is related to the ratio of nanoparticles vs. enzyme in solution. Generally, the more enzyme, the larger the clusters become. For optimal activities and to limit diffusion hindrance of the substrates and products, the clusters should generally be larger than about 200 nm.

The magnetic nanoparticles or aggregates thereof or BNCs thereof may also be coated with a noble metal, such as gold, platinum, or palladium. Alternatively, or in addition, the magnetic nanoparticles or aggregates thereof or BNCs thereof may be coated with a metal oxide layer (e.g., silica or titania) or polymeric protective coating to protect against oxidation of the magnetic nanoparticles. Any suitable method for coating the magnetic nanoparticles may be used. For example, in particular embodiments, magnetic nanoparticles are dispersed in a solution containing a noble metal salt, and the noble metal salt subjected to reducing conditions. The foregoing method can be facilitated by binding difunctional molecules onto the surface of the magnetic nanoparticles before the noble metal salt is reduced. The bifunctional molecules used for this purpose should contain a portion useful for binding to the magnetic nanoparticles (as described above) as well as a noble metal binding portion (e.g., an amine, thiol, phosphine, or chelating moiety) for binding noble metal ions. Optionally, once metal ions are bound to the nanoparticle surface, the magnetic nanoparticles can be washed of excess noble metal salt (e.g., by magnetic capture, filtration, or decanting). Since noble metal ions are attached to the surface, the foregoing methodology provides a more selective method for producing a noble metal coating (i.e., without concomitant production of noble metal nanoparticles) as well as a more uniform coating. In some embodiments, the noble metal coating is applied before enzyme is included with the magnetic nanoparticles, in which case enzyme is later bonded to the noble metal coating. The enzyme can be bonded to the noble metal coating by, for example, functionalizing the noble metal coating with difunctional molecules that bind to the noble metal coating and possess another reactive group for binding to the enzyme.

In another aspect, the invention is directed to a method for producing a hierarchical catalyst assembly containing the BNCs incorporated into a macroporous scaffold, as described above. In typical embodiments, the BNCs or noble-metal coated versions thereof, are made to adsorb onto the surface of a macroporous scaffold by contacting the BNCs or noble-metal coated versions thereof with the macroporous scaffold in an aqueous-based solution such that the nanoparticles adsorb onto the surface of the macroporous scaffold. In the method, BNCs are generally contacted with the macroporous scaffold in solution (i.e., liquid solution) to substantially embed the BNCs into macropores of the scaffold. The solution can include water and/or any suitable solvent that permits efficient and intimate contact between the BNCs and scaffold. Typically, the BNCs will adsorb onto or into the scaffold by self-assembly mechanisms, i.e., by magnetic interaction, physisorption, and/or chemisorption. After the BNCs have been embedded into the scaffold, the catalyst assembly may be used without further processing, or the catalyst assembly may be rinsed in water or a suitable solvent, or stored before use, e.g., in a solution suitable for preserving the enzyme. In some embodiments, the BNCs are adhered onto the surface of magnetic microparticles, and the BNC-microparticle assembly embedded into a continuous macroporous scaffold.

The templating of the BNCs onto macroporous scaffolds can be performed in the same buffer as used for BNC formation. Small quantities of macroporous scaffolds are typically added sequentially to the BNCs until the supernatant is clear, which indicates that all the BNCs have been trapped on the surface of the scaffolds. The color of the supernatant is generally monitored by the absorbance of the nanoparticle clusters after capture of the BNC-loaded scaffolds with small electromagnets. The quantity of scaffold needed to capture BNCs depends on the mass magnetization and the surface area of the scaffold. Alternatively, the binding capacity of the scaffold can be determined and the appropriate amount of BNCs added for complete capture. To increase the mass magnetization of the material in solution, BNC-functionalized scaffolds can be diluted with non-functionalized scaffolds without changing the concentration of the enzyme needed for the process.

A continuous macroporous scaffold can be prepared by any suitable method. Any process known in the art for incorporating macropores into a material are considered herein. In particular embodiments, the continuous macroporous scaffold is produced by a templating (templation) process that includes: (i) producing a composite containing a scaffold precursor material or composition having a sacrificial templating agent embedded therein, and (ii) selective removal of the sacrificial templating agent to produce macropores in the scaffold precursor material. In a first set of embodiments, the templating process employs a solvent as the templating agent, wherein the solvent is embedded in the scaffold precursor material. In the solvent templation process, the composite containing the scaffold precursor material with embedded solvent is cooled until the embedded solvent freezes to form solvent crystals, and then the frozen solvent is removed by either evaporation or sublimation to produce macropores in the scaffold precursor material.

When the solvent is water, the solvent templation process can be referred to as an ice templation process. In a second set of embodiments, the templating process employs a solid sacrificial templating agent that is embedded in the scaffold precursor material. The sacrificial templating agent can be, for example, a polymeric or metal oxide substance that can be selectively removed after incorporation into the scaffold precursor. The incorporation of such sacrificial templating agents are well known in the art. By methods well known in the art, the sacrificial templating agent can be selectively removed by, for example, acid or base leaching, solvent dissolution, or pyrolytic decomposition. In other embodiments, the sacrificial templating agent is a burn-out material, which is a material that either volatilizes or decomposes upon application of sufficient heat to produce the macropores.

Further details of macropore-forming methods conventionally used in the art can be found in, for example, L. Yang, et al., "Robust Macroporous Materials of Chiral Polyaniline Composites", *Chem. Mater.*, 18(2), pp. 297-3000 (2006); M. Abdullah, et al., "Preparation of Oxide *Particles with Ordered Macropores by Colloidal Templating and Spray Pyrolysis*", *Acta Materialia*, 52, pp. 5151-5156 (2004); T. Niu et al., "Preparation of Meso-Macroporous A-Alumina Using Carbon Nanotube as the Template for the Mesopore and Their Application to the Preferential Oxidation of CO in $H_2$-Rich Gases", *Journal of Porous Materials*, vol. 20, issue 4, pp. 789-798 (2013); and M. Davis, et al., "Formation of Three-Dimensional Ordered Hierarchically Porous Metal Oxides via a Hybridized Epoxide Assisted/Colloidal Crystal Templating Approach", *ACS Appl. Mater. Interfaces*, 5(16), pp. 7786-7792 (2013), all of which are herein incorporated by reference in their entirety.

Figure 1B:
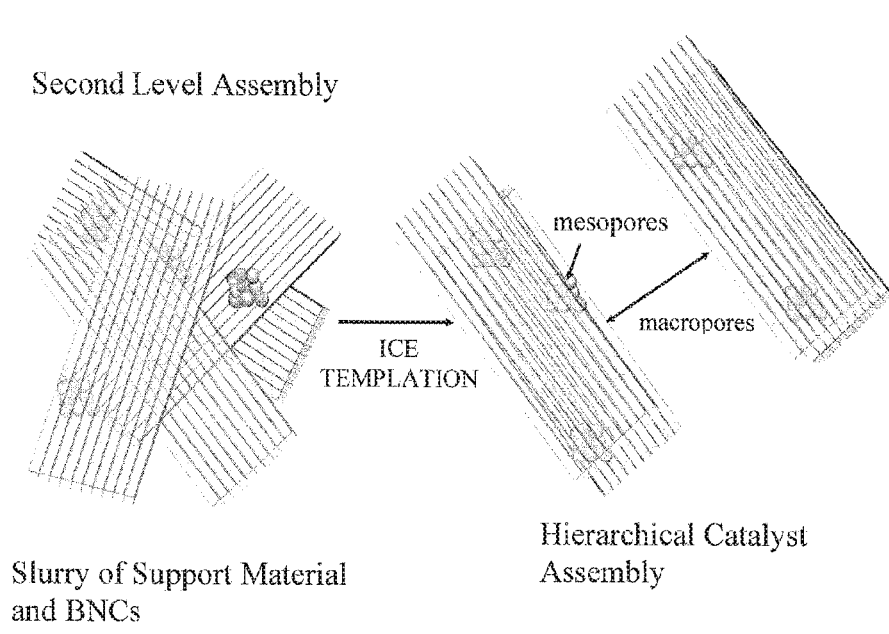

FIGS. 1A and 1B depict an exemplary process for producing first and second levels of assembly, respectively, in a hierarchical catalyst assembly. FIG. 1A shows an exemplary process for forming a first level of assembly of a hierarchical catalyst assembly containing BNCs composed of mesoporous aggregates of magnetic nanoparticles and horseradish peroxidase. FIG. 1B shows an exemplary process for forming a second level of assembly by incorporating the BNCs of FIG. 1A into a macroporous scaffold composed of an ice-templated continuous material, such as a polymeric material, such as a biopolymer, which may be a polysaccharide, such as cellulose. In some embodiments, the scaffold material may be sonicated before use in order to untangle or disperse individual sheets, fibers, or ribbons of the material. The ice-templating approach described above can be applied to other polymers, such as, for example, chitosan, agars, and polymeric resins.

In another aspect, the invention is directed to a process for depolymerizing lignin, i.e., a lignin depolymerization process, in which any of the BNCs or BNC-scaffold structures described above is used for depolymerizing or facilitating the depolymerization of lignin. The lignin being depolymerized can be any lignin-containing material. The precursor lignin can be any of a wide variety of lignin compositions found in nature or as known in the art.

As known in the art, there is no uniform lignin composition found in nature. Lignin is a random polymer that shows significant compositional variation between plant species. Many other conditions, such as environmental conditions, age, and method of processing, influence the lignin composition. Lignins differ mainly in the ratio of three alcohol units, i.e., p-coumaryl alcohol, guaiacyl alcohol, and sinapyl alcohol. The polymerization of p-coumaryl alcohol, coniferyl alcohol, and sinapyl alcohol forms the p-hydroxyphenyl (H), guaiacyl (G) and syringyl (S) components of the lignin polymer, respectively. The precursor lignin can have any of a wide variety of relative weight percents (wt %) of H, G, and S components. Besides the natural variation of lignins, there can be further compositional variation based on the manner in which the lignin has been processed. For example, the precursor lignin can be a Kraft lignin, sulfite lignin (i.e., lignosulfonate), or a sulfur-free lignin.

Lignin is the most abundant aromatic based biopolymer on Earth, but it is chemically recalcitrant to conversion and bioconversion due to the apparent randomness of its chemical composition and physical structure. Lignin can be considered a "glue" or "epoxy" between polysaccharide fibers that provides strength, rigidity, and protection to the cell walls of vascular plants. From a chemical standpoint, lignin is a highly heterogeneous polymer formed by the polymerization of phenyl-propanoid molecules including coniferyl, sinapyl and coumaryl alcohols via aryl linkages, ether linkages, and carbon-carbon bonds.

Based on the assumption that 100 gallons of ethanol are produced from 1 ton of biomass and that biomass (e.g., wood and grass) contains on average about 20% lignin, one can quickly estimate that a biorefinery operating on a 100 million gallon per year capacity would produce about 200,000 tons of lignin material. To meet a 20% replacement of gasoline for the U.S. only by 2020, equivalent to about 35 billion gallons of ethanol, a total of approximately 700 million tons of lignin would be produced per year. The actual production of lignin, mostly Kraft lignin as byproduct of the paper industry, is approximately 90 million tons per year worldwide. In other words, the lignin production worldwide would be increased by more than an order of magnitude.

Lignin can be used for low- or high-priced products based on the application and the degree of chemical purity. Until recently, markets for lignin products have not been large, competitive, or attractive enough to compensate for the cost of isolation and purification compared to the recovered energy derived from its burning. This is mainly because the cost of oil is still low enough and the supplies are high enough to provide the building blocks for the chemical and material industries. However, in a carbohydrate economy framework based on biofuels and bioproducts co-production, high-purity isolated lignin dedicated for conversion could be estimated at $1.10 per kg of raw material compared to $0.04, when used for co-firing. Low-end applications are mostly directed to dispersants, soil conditioners for carbon sequestration, adsorbents for fertilizers and pesticides, as well as fuels, which require little or no further conversion after extraction. High-end applications requiring depolymerization of lignin include the production of phenolic precursors (e.g., DMSO, vanillin, phenol, and aromatic compounds) and polymer components (e.g., epoxy resins, polyurethane foams, phenolic resins powders, carbon fibers and glue and binders).

In nature, the conversion of lignin is performed by specialist microbes, particularly fungi and bacteria. Lignocellulosic bacteria and fungus have the ability to depolymerize lignin in order to gain access to cellulosic fractions of biomass. To that end, lignocellulosic bacteria and fungus excrete an array of oxidoreductase enzymes, which include laccases, oxidases, and peroxidases, along with organic acids and $H_2O_2$-producing catalases. The most potent oxidoreductase enzymes are produced by a specific group of fungi known as white rot fungi, which specialize in lignocellulosic degradation. Various types of fungal peroxidases differ in the nature of their substrates.

Lignin peroxidase (LiP, E.C. 1.11.1.14) catalyzes the oxidative cleavage of C—C bonds in a number of model compounds, and oxidizes benzyl alcohols to aldehydes or ketones. Typical reactions catalyzed by lignin peroxidases are Cα-Cα cleavage, Cα oxidation, alkyl aryl cleavage, aromatic ring cleavage, demethylation, hydroxylation and polymerization. Lignin peroxidases are involved in the oxidative breakdown of lignin in white-rot basidiomycetes. Lignin peroxidase catalyzes the oxidation of non-phenolic aromatic rings into aryl cation radicals by $H_2O_2$. A typical example is the oxidation of veratryl alcohol (3,4-dimethoxybenzyl alcohol) into veratryl aldehyde (3,4-dimethoxybenz aldehyde) via the intermediary formation of veratryl cation and benzyl radicals: veratryl alcohol+$H_2O_2$→veratryl aldehyde+$2H_2O$. Manganese peroxidase (MnP; E.C. 1.11.1.13) has lower redox potentials (up to 1.1 V) than LiP (up to 1.5 V) and catalyzes the Mn-mediated oxidation of lignin and phenolic compounds. This enzyme catalyzes the oxidation of Mn(II) to Mn(III) by $H_2O_2$. The highly reactive Mn(III) is stabilized via chelation in the presence of dicarboxylic acid: $2Mn(II)+2H^++H_2O_2 \rightarrow 2Mn(III)+2H_2O$. The purpose of MnP is to generate small and potent oxidizing agents that diffuse into the lignified cell wall and achieve depolymerization of lignin from within. Versatile peroxidase (syn. hybrid peroxidase, manganese-lignin peroxidase: VeP EC 1.11.1.16) is a fairly new ligninolytic enzyme, combining catalytic properties of manganese peroxidase (oxidation of Mn(II)), lignin peroxidase (Mn-independent oxidation of non-phenolic aromatic compounds) and plant peroxidase (oxidation of hydroquinones and substituted phenols). Any one or a combination of the above-mentioned peroxidases may be used in the lignin depolymerization process described herein.

In a first embodiment, the lignin-containing material is a form of lignin partially or substantially separated from other components of wood (e.g., cellulosic and hemicellulosic components), as is generally provided from a pretreatment process of lignocellulosic material, the details of which are well known in the art of lignocellulosic processing and conversion. The pretreatment process serves to either separate lignin from other components of the lignin-containing source, or to weaken the bonds between lignin and the other components. As is also well known in the art, the lignin may be further isolated by, for example, extraction. In a second embodiment, the lignin-containing material is a lignin-containing consumable product, such as paper or cardboard, which may or may not be pretreated. In a third embodiment, the lignin-containing material is a lignin-containing natural source (i.e., raw lignocellulosic material), such as woodchips, grasses (e.g., switchgrass and mixed grasses), corn stover (e.g., leaves, husks, stalks, or cobs of corn plants), sugarcane, saw dust, hemp, or a combination thereof, all of which are generally pretreated to make the lignin sufficiently available for depolymerization.

In the lignin depolymerization process, any of the BNC or BNC-scaffold structures, described above, is contacted with a lignin-containing material under conditions where partial or complete depolymerization of lignin occurs by free-radical activity of the enzyme-bound magnetic nanoparticles or aggregates thereof. The BNC or BNC-scaffold structure and the lignin-containing material are generally made to contact by combining them in an aqueous solution, such as an aqueous solution used in a pretreatment process of the lignin-containing material. In some embodiments, a room temperature condition (e.g., at least 10, 15, 18, 20, or 22° C. and up to 25° C., 30° C., or 40° C., or any range therein) is used during the depolymerization process. In other embodiments, an elevated temperature condition (e.g., above 40° C., or at least or above 45, 50, or 60° C., or up to the temperature that the FRP enzyme degrades or suffers a substantial loss in activity) is used during the depolymerization process. In other embodiments, a reduced temperature condition (e.g., below 15° C., or up to or below 10, 5, or 0° C.) is used during the depolymerization process. By being depolymerized, the lignin is broken down into shorter segments compared to its original form. A complete depolymerization results in the conversion of all or a substantial portion (e.g., at least 80, 90, or 95%) of the lignin into at least one or more of the basic building blocks of lignin, i.e., coniferyl, sinapyl, and coumaryl alcohols, and derivatives thereof. A partial depolymerization generally results in less than 80%, or up to 70, 60, 50, 40, 30, 20, 10, 5, or 1% of lignin being converted to primary building blocks, with the rest of the lignin being converted to segments containing two, three, four, or a higher multiplicity (even up to 10, 20, 50, 100, 200, 500, or 1000) of building blocks (e.g., p-hydroxyphenyl, guaiacyl, and syringyl units derived from coumaryl, coniferyl, and sinapyl alcohols, respectively). Since different degrees of lignin depolymerization may be preferred for different applications, the depolymerization conditions can be suitably adjusted to provide an appropriate degree of depolymerization or to favor one or more types of depolymerization products over others.

Since each lignin-containing material has a different distribution and relative amount of each building block, the relative amount of each product produced from depolymerization is very much dependent on the type of lignin-containing material. Other depolymerization products, e.g., aromatic aldehydes, ketones, alcohols, and acids, are generally also produced during the polymerization process, typically in lesser amounts. In embodiments where such other products are not desired, they may be advantageously minimized or eliminated as a product by adjustment of reaction conditions, including appropriate selection of the FRP-bound magnetic nanoparticle or aggregate thereof.

Any of the BNC or BNC-scaffold structures described above can be used for the lignin depolymerization process. In particular embodiments, the enzyme used in the lignin depolymerization process is a FRP, such as a peroxidase, and particularly, a lignin-degrading peroxidase, such as a lignin peroxidase, versatile peroxidase, manganese peroxidase, or combination thereof (including a core-shell combination thereof). The FRP enzyme may also more particularly be a fungal, microbial, or plant peroxidase. In specific embodiments, the FRP enzyme is a system of two FRP enzymes, such as a peroxidase combined with a glucose oxidase, or a peroxidase and/or oxidase combined with a laccase.

In some embodiments, the lignin depolymerization process is coupled (i.e., integrated) with a downstream process in which depolymerization product produced in the lignin depolymerization process is used for the production of other products. The downstream process may convert lignin depolymerization product into, for example, biofuel or an industrial chemical product, e.g., a polymer, plastic, polymer precursor (monomer), solvent, adhesive, paint, detergent, lubricant, food product, medicinal product, or aroma, or a precursor therefore. The downstream process may alternatively incorporate the lignin depolymerization product into any such end product.

In some embodiments, the lignin depolymerization process is coupled with an upstream process in which lignin-containing material is provided for use in the lignin depolymerization process described herein. The upstream process can be, for example, a paper or pulp producing process, a biomass-to-biofuel process (i.e., where primarily cellulosic material is hydrolyzed and converted to biofuel), or a biomass-to-ethanol fermentation process (i.e., where primarily cellulosic material is hydrolyzed and converted to ethanol).

In another aspect, the invention is directed to a process for removing aromatic contaminants from water (i.e., a water remediation process). In the process, water contaminated with one or more aromatic substances is contacted with any of the BNC or BNC-scaffold structures, described above, to cause the aromatic substances to precipitate, i.e., as insoluble material. The precipitated (i.e., sedimented) material is preferably then further separated, such as by centrifugation or settling, and removed from the water by, for example, filtration or decanting. Without being bound by any theory, it is believed that the aromatic substances react with free radicals produced by the enzyme-bound magnetic nanoparticles to produce a polymerized material derived from the aromatic substances. The aromatic contaminant can be any aromatic substance, including those more commonly found in contaminated water. In some embodiments, the aromatic contaminant is benzene, or a benzene derivative, such as a halogenated benzene (e.g., chlorobenzene, dichlorobenzenes, bromobenzenes, or a polychlorinated biphenyl, i.e., PCB), alkylbenzene (e.g., toluene, ethylbenzene, or a xylene), phenolic substance (e.g., phenol, resorcinol, catechol, a polyphenol, or a substituted phenol, such as cresol), etherified benzene (e.g., anisole), fused ring compound (e.g., naphthalene, or polyaromatic hydrocarbon), aromatic amine (e.g., aniline and N-alkyl or N,N-dialkyl substituted anilines), benzoic acid compound (e.g., benzoic acid, esters thereof, and hydroxy-substituted derivatives of benzoic acid), or bioactive aromatic compound (e.g., as produced by bacteria, fungi, or plants). In other embodiments, the aromatic contaminant is a heteroaromatic substance, such as furan, pyran, dioxin, thiophene, pyridine, pyrazine, pyrimidine, pyrrole, imidazole, indole, and derivatives thereof.

Any of the BNC or BNC-scaffold structures described above can be used for the water remediation process. In particular embodiments, the enzyme used in the water remediation process is a FRP enzyme, such as horseradish peroxidase, or horseradish peroxidase in combination with an oxidase.

In another aspect, the invention is directed to a process for polymerizing monomers polymerizable by a free-radical mechanism. In the process, one or more types of monomers are reacted with any of the BNC or BNC-scaffold structures, described above, to cause the monomers to polymerize. The monomers can be, for example, any of the substances provided above for the water remediation process. In particular embodiments, the monomers are or include vinyl-addition monomers. Upon polymerization, a vinyl-addition polymer is produced. Some examples of such monomers include ethylene, propylene, butadiene, the acrylates and esters thereof, methacrylates and esters thereof, acrylonitriles, vinyl acetate, styrene, divinylbenzene, vinyl fluorides, and vinyl chlorides. In other embodiments, the monomers are phenolic compounds. Upon polymerization, a phenolic resin or polymer is produced. The polymerization process can utilize any of the conditions and apparatuses well known in the art for practicing polymerization reactions, and in particular, free-radical initiated polymerization reactions.

In another aspect, the invention is directed to a process for the epoxidation of alkenes. In the process, alkenes in the presence of oxygen are reacted with any of the BNC or BNC-scaffold structures, described above, provided that the BNC or BNC-scaffold structure includes an oxygen-transfer enzyme, such as a chloroperoxidase or lipase enzyme. The reaction is advantageously conducted at a significantly lower temperature (e.g., room temperature, ca. 25° C.) compared to temperatures conventionally used in the art for epoxidizing alkenes. The alkene can be, for example, ethylene or propylene, and the end product can be, for example, ethylene oxide or propylene oxide.

In particular embodiments, the epoxidation process employs immobilized chloroperoxidase or lipase, or both, in BNCs immobilized onto magnetic scaffolds. The enzyme-containing catalysts may be used with magnetic reactors (i.e., by magnet trap methods, as further described below) either in a continuous flow or batch system. In continuous flow systems, the catalysts are retained in the reactors by the magnetic field of the electromagnets. The reagents (alkene and oxidant) are introduced upstream and react with the enzymes in the reaction zone. The oxidant can be, for example, hydrogen peroxide or glucose if the chloroperoxidase is used with a glucose oxidase. The solution can be aqueous or organic (such as dioxane) or any other solvent compatible with the enzyme. The continuous flow removes the products of the reaction from the vicinity of the enzymes and prevents the accumulation of inhibitory levels of substrates and products. The products are typically concentrated downstream of the conversion process, due to difference in solubility, and subsequently reacted in a secondary reaction due to the poor stability of epoxide groups. In batch systems, the reagents are generally mixed with the catalysts, stirred, and the catalysts removed from the batch by magnetic capture when the reaction is complete. The products of the reactions are concentrated due to a difference in solubility, and then subsequently reacted. The captured catalysts can be reused for a new batch reaction.

In another aspect, the invention is directed to a process for the halogenation of phenols. In the process, phenols are reacted with any of the BNC or BNC-scaffold structures, described above, provided that the BNC or BNC-scaffold structure includes a halogenating enzyme, such as a chloroperoxidase. The phenol reactant can be phenol itself, or any suitable phenol derivative, such as any of the phenolic compounds provided above. The phenolic product can be, for example, a chlorinated, brominated, or iodated phenol compound.

In particular embodiments, the halogenation process employs immobilized chloroperoxidase in BNCs immobilized onto magnetic scaffolds. The enzyme-containing catalysts may be used with magnetic reactors (i.e., by magnet trap methods, as further described below) either in a continuous flow or batch system. In continuous flow systems, the catalysts are retained in the reactors by the magnetic field of the electromagnets. The reagents (phenol or phenol derivatives, oxidant, and halide ions, such as I$^-$, Br$^-$ or Cl$^-$) are introduced upstream and react with the enzymes in the reaction zone. The oxidant can be, for example, hydrogen peroxide or glucose if the chloroperoxidase is used with a glucose oxidase. The solution can be aqueous or organic (such as dioxane) or any other solvent compatible with the enzyme. The continuous flow removes the products of the reaction from the vicinity of the enzymes and prevents the accumulation of inhibitory levels of substrates and products. The products are typically concentrated downstream of the conversion process due to the difference in volatility and solubility. In batch systems, the reagents are generally mixed with the catalysts, stirred, and the catalysts removed from the batch by magnetic capture when the reaction is complete. The products of the reactions are concentrated due to a difference in volatility and solubility. The captured catalysts can be reused for a new batch reaction.

In another aspect, the invention is directed to a process for inhibiting growth and function of microorganisms in a solution. In the process, water containing microorganisms (i.e., microbial-contaminated water) is treated with any of the BNC or BNC-scaffold structures, described above, provided that the BNC or BNC-scaffold structure includes an FRP enzyme, such as a peroxidase, or more specifically, a lactoperoxidase (LPO) or a lactoperoxidase combined with a glucose oxidase.

The LPO-system is considered to be one of the body's natural defense mechanisms against microbial infections since LPO exhibits broad antifungal and antibacterial activity in the presence of thiocyanate and hydrogen peroxide. Consequently, applications of lactoperoxidase are being found in preserving food, cosmetics, and ophthalmic solutions. Furthermore, lactoperoxidase have found applications in dental and wound treatment. Lactoperoxidase may also find application as anti-tumor and antiviral agents. Lactoperoxidase substrates include bromide, iodide and thiocyanate. The oxidized products produced through the action of this enzyme have potent bactericidal activities. The lactoperoxidase catalysts can be used in combination with magnetic trap reactors, described below, to produce the broadly acting hypothiocyanite, hypobromite, and hypoiodite ions from thiocyanate, bromide, and iodite respectively. These ions are then released with the effluent where they induce oxidative stress to the microorganisms downstream, thereby decontaminating the effluent. Alternatively, the catalysts can be used in a batch reactor or onto a surface in an aqueous solution and then recaptured by a magnetized collector. The action of hypothiocyanate, for example, against bacteria is reported to be caused by sulfhydryl (SH) oxidation. The oxidation of —SH groups in the bacterial cytoplasmic membrane results in loss of the ability to transport glucose and also in leaking of potassium ions, amino acids, and peptide, thereby inducing the death of the microorganisms. The products of lactoperoxidase are generally considered safe and non-mutagenic, and hence compatible with food and health applications.

In another aspect, the invention is directed to a process for converting carbon dioxide to methanol. In the process, carbon dioxide is reacted with any of the BNC or BNC-scaffold structures, described above, provided that the BNC or BNC-scaffold structure includes a dehydrogenase system containing at least two, three, or at least four dehydrogenase enzymes. The dehydrogenase enzyme system can include, for example, a formate dehydrogenase (NAD$^+$ oxidoreductase, such as EC 1.2.1.2; or ferricytochrome-b1 oxidoreductase, such as EC 1.2.2.1), combined with a formaldehyde dehydrogenase (e.g., EC 1.2.1.2) or a cytochrome in formate:ferricytochrome-b1 oxidoreductase (e.g., EC 1.2.2.1); an alcohol dehydrogenase (EC 1.1.1.1); and glucose dehydrogenase (EC 1.1.99.10).

The carbon dioxide is converted to formic acid by the formate dehydrogenase, the formic acid is converted to formaldehyde by the formaldehyde dehydrogenase, and the formaldehyde is converted to methanol by an alcohol dehydrogenase. A glucose dehydrogenase is recycling the NAD$^+$ cofactors from the formate dehydrogenase, formaldehyde dehydrogenase, and alcohol dehydrogenase reaction with their substrates ($CO_2$, formic acid, and/or formaldehyde) and NADH. The theoretical molar ratio is three molecules of glucose to convert one molecule of $CO_2$ to methanol. In particular embodiments, the formate dehydrogenase, formaldehyde dehydrogenase, and alcohol dehydrogenase are entrapped individually or together inside the BNCs. The BNCs are then templated onto the magnetic scaffold. The BNCs made with the glucose dehydrogenase are then added to the previous catalysts. This configuration permits the trapping and recycling of cofactors and maximizes their use at the vicinity of the formate dehydrogenase, formaldehyde dehydrogenase, and alcohol dehydrogenase.

Alternatively, the $CO_2$ conversion process can be decoupled with three distinct sequential reactions using the formate dehydrogenase and glucose dehydrogenase catalysts for the synthesis of formic acid from $CO_2$, then formaldehyde dehydrogenase and glucose dehydrogenase catalysts for the synthesis of formaldehyde from formic acid, then alcohol dehydrogenase and glucose dehydrogenase for the synthesis of methanol from formaldehyde. Separate reaction zones in flow reactors or separate batch processes can be used. Hence, the process can be used to produce formic acid, formaldehyde, and/or methanol.

For any of the processes described above, the BNC-scaffold structures can advantageously be captured by magnetic separation in order to prevent contamination of the final product. Moreover, a further advantage of the BNC-scaffold structures described herein is their ability in many cases to retain their activity and re-form after capture, which permits them to be re-used after capture, thereby increasing the total turnover number (TTN) of the enzymes. BNC-scaffold systems showing a loss of activity after several cycles can advantageously be easily extracted and concentrated to their solid form to provide a less wasteful and more efficient process. In particular, metal-coated BNCs can be repurposed by denaturation of the enzymes, sonication, and purification in order to be restored and re-used with fresh functional enzymes. BNC-scaffold structures are attractive for process applications that use lower intensity magnetic fields. The BNC-scaffold structures maintain stable, nano-sized, and mesoporous structures, which helps to maintain enzyme activity while increasing the overall density and mass susceptibility of the magnetic catalyst. These ultra-structures lend themselves to easier manipulation by external magnetic fields as produced by permanent small magnets and weak field electromagnets. The reaction solution can be purged and replaced while the BNC-scaffold structures are magnetically trapped, hence allowing for sequential use of the BNC-scaffold structures as long as the enzyme retains process level activities.

In yet another aspect, the invention is directed to a magnetic trap method for increasing a space time yield and/or total turnover number of a liquid-phase chemical reaction that includes magnetic particles to facilitate the chemical reaction. In the method, a liquid-phase chemical reaction that includes any of the BNCs or BNC-scaffold structures described above is subjected to a plurality of magnetic fields (i.e., "dynamic magnetic trap reactors" or "DMTRs") by one or a plurality of electromagnets, each of which may be independently adjusted to provide a magnetic field of desired magnetic strength, relative position in the liquid-phase chemical reaction, and relative motion to spatially confine the magnetic particles. In the method, the magnetic strength, relative positioning, and relative motion of the plurality of magnetic fields are provided by a system of electromagnets in which current flow is appropriately controlled or adjusted. In particular, the space time yield can be increased by applying the magnetic fields in a manner that confines the reaction volume space.

Any of the BNCs or hierarchical catalyst assemblies thereof, described above, can be used in the magnet trap method. In particular embodiments, the BNCs or hierarchical catalyst assemblies thereof advantageously behave in a "fluidic" manner during the course of the reaction while under the influence of the moving external magnetic fields. The fluidic motion can be characterized by a congregation (i.e., "cloud") of the BNCs or hierarchical catalyst assemblies collapsing at impact with the wall of the reactor when attracted by the electromagnets. By doing so, the products of the reaction of the enzymes are expelled from the catalysts. When the "cloud" is moving in the other direction, it absorbs fresh substrate, which reacts with the enzymes, and then the products are expelled again when the "cloud" hits the opposite wall. This is a significant feature of the magnetic scaffolds since this behavior can permit them to function as a "micropump" (i.e., similar to squeezing a sponge).

In some embodiments, the confinement results in at least a first and second reaction zone in which separate reactions can be conducted in each reaction zone. The purpose of the foregoing embodiments is to avoid the accumulation of substrates and products in the vicinity of the catalysts. The free radicals generated by the enzymes are highly reactive and can react with the enzymes or polymerize at the surfaces of the catalysts. To avoid such conditions that would be detrimental to the overall process and efficiency of the enzymes, the process is decoupled in a reaction volume 1 where the free radicals are generated, and a reaction volume 2, void of catalyst, where they react with each other. The magnetic catalysts are maintained in the reaction volume 1 by the alternating magnetic field generated by the electromagnets while the solution and the reagents flow through the catalysts, react, and are carried away by the flow. The parameters controlling the process are primarily the intensity of the induced magnetic field and the frequency of the bouncing motion that confine the magnetic catalysts and the flow rate of the solution in the reactor.

In other embodiments, the magnetic trap method includes magnetic capture of the magnetic particles by using the dynamic magnetic trap reactors after the reaction has reached completion. In this configuration, the electromagnets are turned on in order to capture all of the magnetic catalyst. The solution containing the products of the reaction is typically removed or flushed out for further processing. The batch is generally replenished with fresh solution with the substrates to be converted. Typically, the electromagnet arrays resume the cycling power on/power off to agitate the magnetic catalysts in the batch. When the catalysts are reaching their end-usage, they can be captured by the electromagnets, and the reactor can be filled up with rinsing solution. The electromagnets can then be turned off to free the magnetic catalysts that are flushed out with the rinsing solution. The magnetic catalysts can be concentrated and extracted from the rinsing solution with a secondary array of electromagnets in a downstream secondary process.

In particular embodiments of the magnetic trap method, current flow to the electromagnets is controlled by a computer program to provide a desired set of magnetic strengths, relative positions in the liquid-phase chemical reaction, and/or relative motions of the plurality of magnetic fields that cause spatial confinement of the magnetic particles. Any desirable number of electromagnets may be used, and the electromagnets can be positioned in any suitable manner around the reaction vessel to achieve, for example, reaction volume confinement, separation of reactions, or magnetic capture of the magnetic particles. The electromagnets may also be arranged in arrays, such as two arrays of two electromagnets, two arrays of three electromagnets, two arrays of four electromagnets, three arrays of two electromagnets, three arrays of three electromagnets, and so on, with each individual electromagnet or each array of electromagnets independently operated and controlled.

Figure 2A:
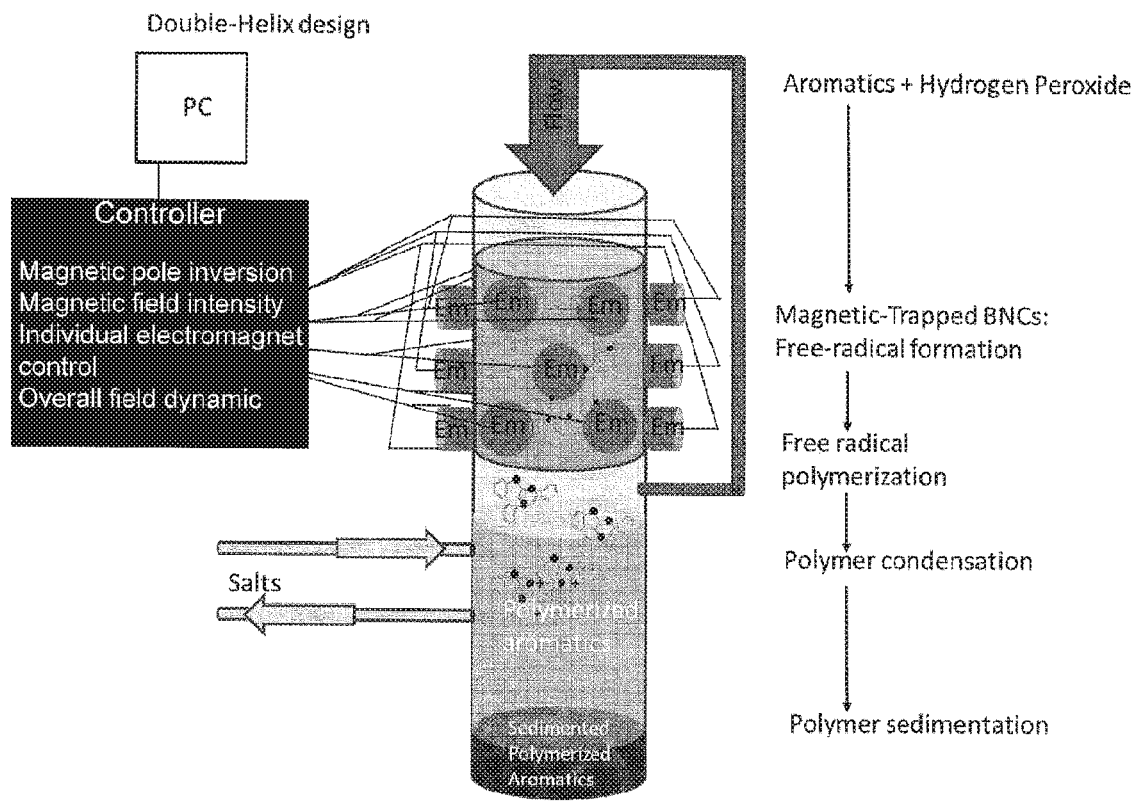
FIGS. 2A, 2B. Single-helix (FIG. 2A) and double-helix (FIG. 2B) magnetic trap arrangements as specifically applied to water remediation and/or free radical polymerization of aromatic compounds.
Figure 2B:
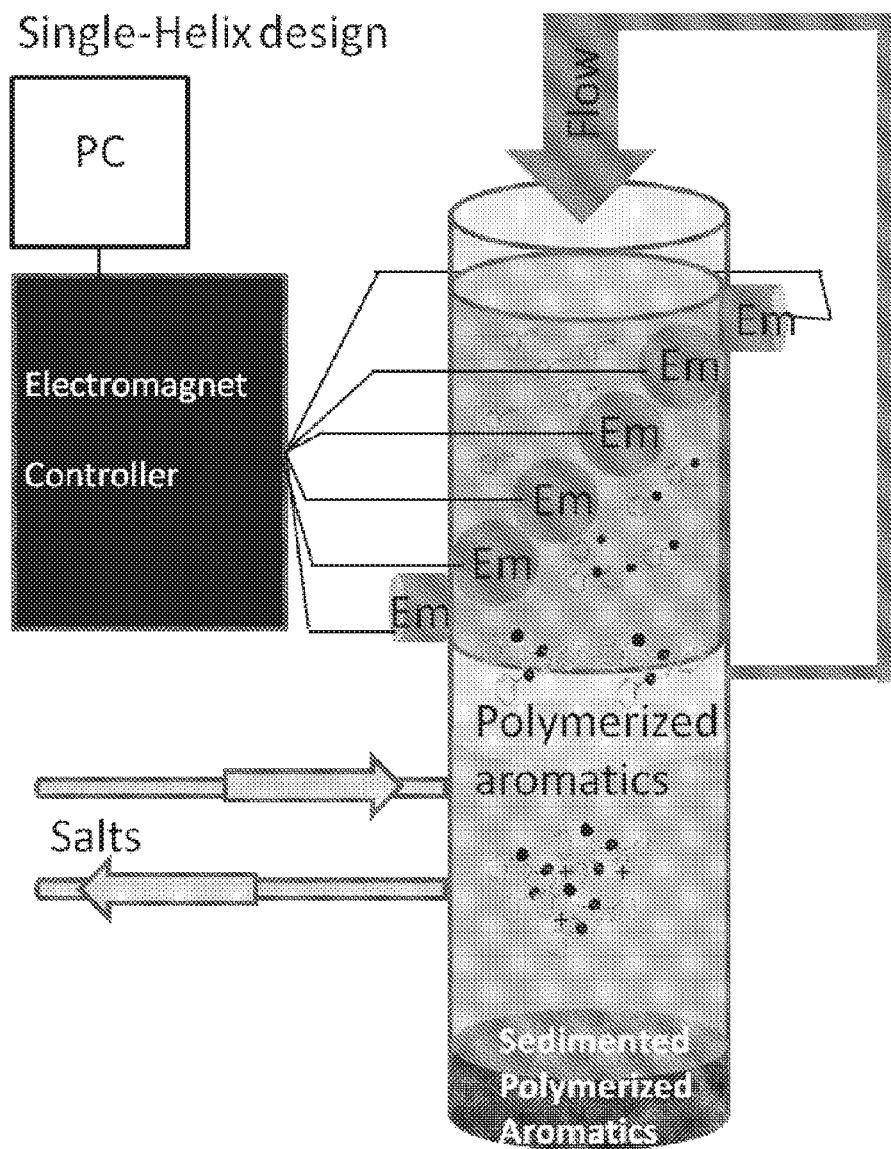

For example, a single-helix or double-helix arrangement of the electromagnets may be used, as particularly depicted in FIGS. 2A and 2B, respectively. The magnetic arrays include computer-controlled and programmable electromagnets that maintain the magnetic catalysts in the reaction zone and prevent the leaching of the enzymes with the solution. As shown in FIGS. 2A and 2B, as particularly applied to the polymerization of aromatics or remediation of water containing such aromatics, the array of electromagnets can be appropriately operated to magnetically trap the BNCs or BNC-scaffold assemblies to promote free radical polymerization in a defined section or plurality of sections of the reaction vessel, while other parts of the reaction volume are available for non-magnetic induced reactions or physical processes, such as polymer condensation or sedimentation. The separation of the oxidation of the aromatics and the polymerization thereof prevent the formation of the polyphenols close to the catalysts. The molecular entrapment of the catalysts (and enzymes) with polyphenol is referred to as product inhibition. Product inhibition by molecular entrapment is irreversible and translates to drastic loss of catalytic efficiency. Moreover, in the separated reactors, polymerization and condensation can be favored in the bottom part of the reactor by inclusion of coagulating agents, such as salts or divalent cations, or by inclusion of coupling surfaces, such as sand or organic materials, that trap the polyphenols and free radicals.

The motion of magnetic fields can be any suitable motion, dependent on the desired result, such as scanning vertical (up and/or down) motion, scanning horizontal (left and/or right) motion (e.g., "ping-pong motion"), figure eight ("8") motion, diagonal up and down ("V") motion, double diagonal (W motion), scanning horizontal, diagonal down scanning horizontal (Z motion). Other types of motion may be desirable to control the motion of the catalysts in solution provided that the flow of liquid is compensated by the counter force generated by the electromagnets. The motion is the result of the geometry of the electromagnets related to the geometry of the reactor and the cycling of the power on/off of the electromagnets. The speed of the catalyst motion is determined by the frequency of the electromagnets (power on/power off) and the strength of the magnetic field from these magnets, which is a function of the current intensity provided to the electromagnets. A computer program can be devised to make any desired motion.

For example, a computer program can be devised to provide an alternating or "ping-pong" motion of the magnetic field. The ping-pong motion is achieved by sequentially turning on one magnet and shutting down its counterpart. An example of such a program for inducing a ping-pong motion is as follows:

```
int period = 1000; //Set the period in msec
void setup( ){
    pinMode(6, OUTPUT); //Set the u-axis output pin pinMode(6, OUTPUT); paired with 9
    pinMode(7, OUTPUT); //Set the u-axis output pin; paired with 10
```

```
  pinMode(8, OUTPUT); //Set the u-axis output pin; paired with 11
  pinMode(9, OUTPUT); //Set the v-axis output pin; paired with 6
  pinMode(10, OUTPUT); //Set the v-axis output pin; paired with 7
  pinMode(11, OUTPUT); //Set the v-axis output pin; paired with 8
}
void loop( ){
  digitalWrite(6, HIGH); //Switch on u-axis
  digitalWrite(7, LOW); //Switch off u-axis
  digitalWrite(8, HIGH); //Switch on u-axis
  digitalWrite(9, LOW); //Switch off v-axis
  digitalWrite(10, HIGH); //Switch on v-axis
  digitalWrite(11, LOW); //Switch off v-axis
  delay(ceil(period/2)); //Delay for the given interval
  digitalWrite(6, LOW); //Switch on u-axis
  digitalWrite(7, HIGH); //Switch off u-axis
  digitalWrite(8, LOW); //Switch on u-axis
  digitalWrite(9, HIGH); //Switch off v-axis
  digitalWrite(10, LOW); //Switch on v-axis
  digitalWrite(11, HIGH); //Switch off v-axis
  delay(ceil(period/2)); //Delay for the given interval
}
```

Figure 3:
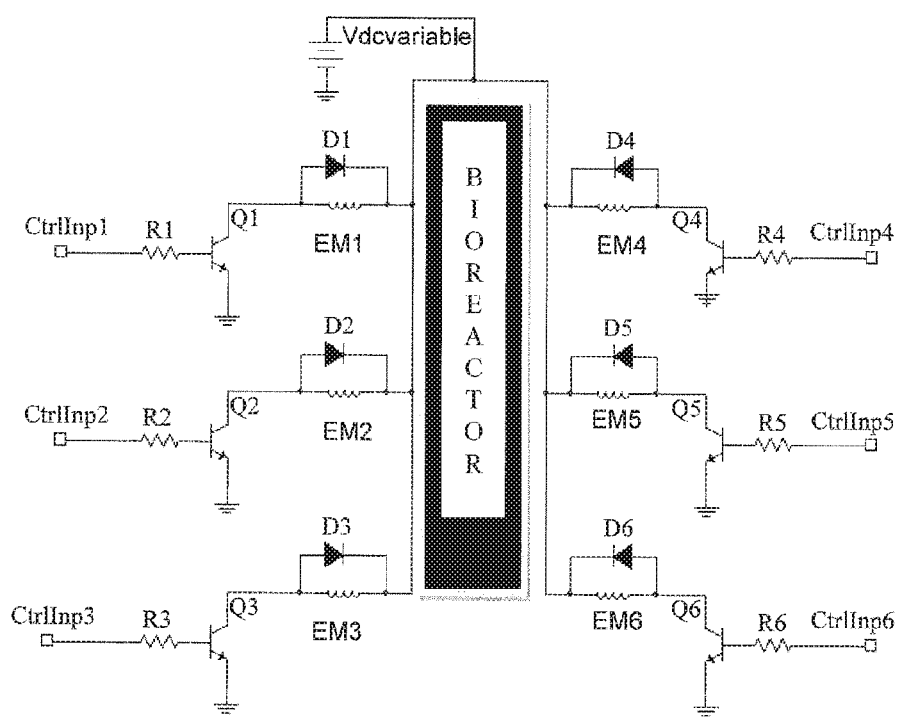
FIG. 3. An electronic diagram for an arrangement of computer-programmable controllers useful in independently controlling six electromagnets or two arrays of three electromagnets.
Figure 4:
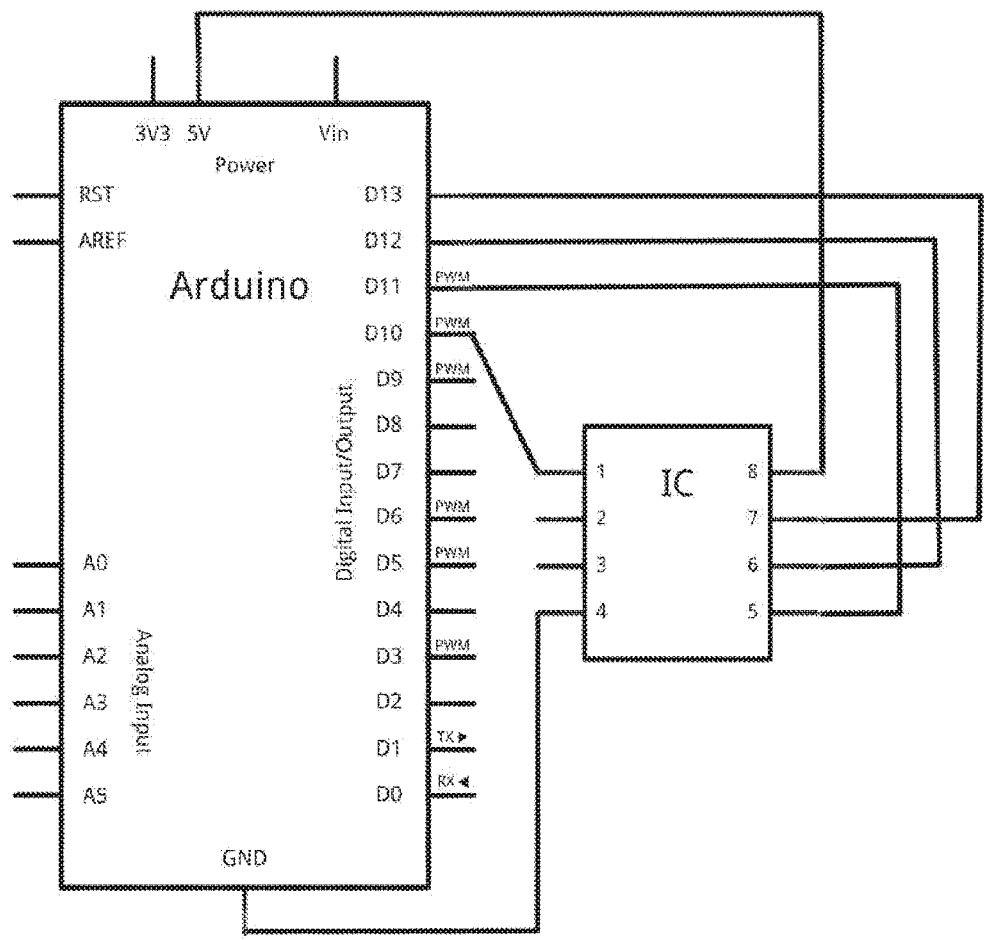
FIG. 4. An exemplary microcontroller for use in the control input ("CtrlInp") components of the electronic arrangement provided in FIG. 3.

The invention is also directed to an apparatus for conducting the magnetic trap method described above. The apparatus should include at least a reaction chamber constructed of a suitable reaction vessel material and having at least two opposing walls; one or more (typically, arrays of) electromagnets arranged on external surfaces of the at least two opposing walls; and a computer-programmable controller for controlling current flow in the electromagnets. The number of electromagnets is scalable based on the controllers being used, or by the use of multiple controllers. The reaction chamber can be designed as, for example, a batch reactor, or alternatively, a flow cell for continuous production. The design and construction of such reaction vessels are well known in the art. In typical embodiments, the apparatus also includes means for individually controlling the electromagnets by use of one or more computer-programmable controllers, which control the frequency of the on/off switch of the electromagnets. The computer-programmable controllers may have the electronic set up shown, for example, in FIG. 3. In the diagram in FIG. 3, the programmable electronic board can employ, for example, a 12 V power source and 6 outputs (+5 V), shown for exemplary purposes only. The microcontroller control inputs ("CtrInp" designations) can be as shown, for example, in FIG. 4, which depicts a typical commercially available controller board (e.g., Arduino™ UNO) that has 14 digital input/output pins (of which six can be used as PWM outputs), six analog inputs, a 16 MHz crystal oscillator, a USB connection, a power jack, an ICSP header, and a reset button. Each output can control an electromagnet or an array of electromagnets. The board is powered by an external power generator providing the 12V source. The output of +5V is against the ground (0/+5V). The USB port is used to program the microcontroller board.

EXAMPLES

Lignin Depolymerization

Figure 5:
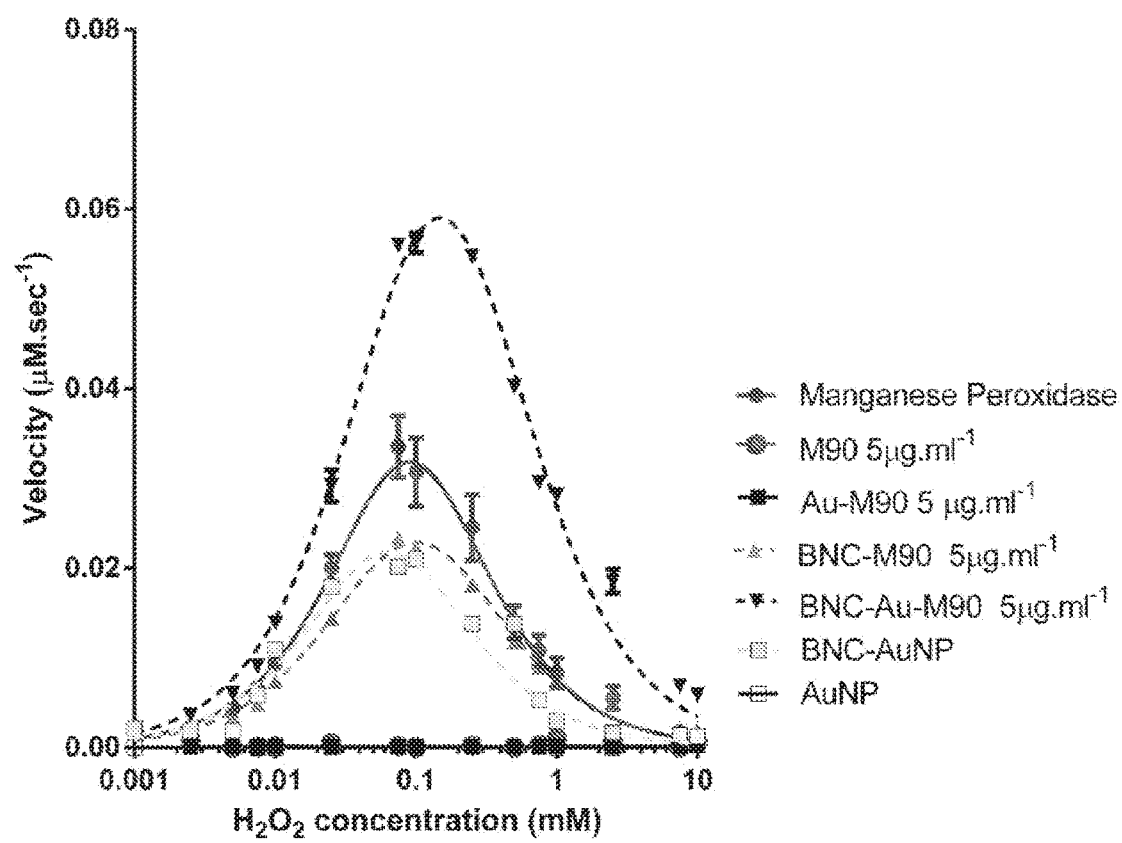
FIG. 5. Graph showing the effect of $H_2O_2$ on DMP oxidation velocity catalyzed by manganese peroxidase at 2.5 nM, Au-M60 at different concentrations, and BNCs thereof at pH 3.5 in malonate buffer (50 mM). The x-axis is on a $\log_{10}$ scale for convenience. The BNCs (gold coated nanoparticles) increase the activity and lower the inhibition of manganese peroxidase.
Figure 6:
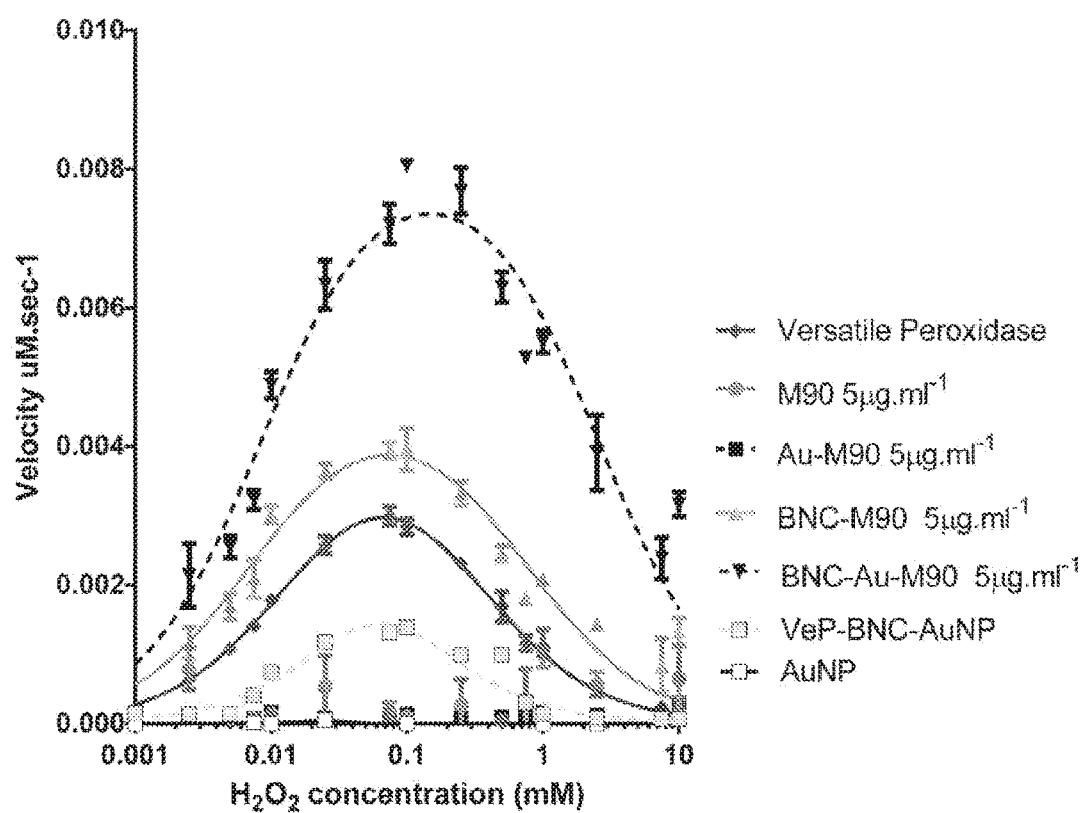
FIG. 6. Graph showing the effect of $H_2O_2$ on DMP oxidation velocity catalyzed by versatile peroxidase at 2.5 nM, Au-M60 at different concentrations, and BNCs thereof at pH 3.5 in malonate buffer (50 mM). The x-axis is on a $\log_{10}$ scale for convenience. The BNCs (gold coated nanoparticles) increase the activity and lower the inhibition of versatile peroxidase FIGS. 7A, 7B. Spectra showing use of manganese peroxidase and versatile peroxidase for lignin depolymerization of biomass feedstock (mixed grasses).

Peroxidase enzymes have been amply investigated due to the potential of their oxidative activity for industrial sectors. Yet, they are particularly prone to substrate-inhibition, which has prevented development of large-scale peroxidase-based biotechnologies. Herein is demonstrated that the activity and resilience of fungal ligninolytic peroxidases can be dramatically increased in association with gold-coated magnetic nanoparticles (Au-MNPs). The assemblies have superior activity than the free enzyme systems and can be applied to the enhanced depolymerization of the lignin component of energy feedstocks. The results show that the assemblies can encompass complex enzyme systems to overcome the current physical and biochemical limitations of this family of enzymes and create a new generation of lignin catalysts. The enzyme-based catalysts exhibited a bimodal activity with two maxima between 0.1 and 1 mM and above 500 mM of $H_2O_2$. The Au-MNPs had no activity in the range of concentration optima for the enzymes. As shown in FIGS. 5 and 6, differences were observed on the initial rates of catalyst made with two types of magnetite nanoparticles, Au-M90 and Au-M60, where Au-M90 had a more pronounced effect on both velocities and optimal $H_2O_2$ concentration. M60 refers to nanoparticles of magnetite formed at 60° C., and M90 refers to magnetite nanoparticles formed at 90° C. The temperature during formation affects the crystallite size and ultimately the magnetic properties for the nanoparticles. M90 nanoparticles are about 10 nm average diameter while M60 nanoparticles are about 8 nm average diameters.

FIG. 5 is a graph showing the effect of $H_2O_2$ on DMP oxidation velocity catalyzed by manganese peroxidase at 2.5 nM, Au-M60 at different concentrations, and BNCs thereof at pH 3.5 in malonate buffer (50 mM). The x-axis is on a $log_{10}$ scale for convenience. The coating with gold prevents the dissolution of the magnetic core (magnetite) in the buffer necessary for enzymes activities. The BNCs (gold coated nanoparticles) increase the activity and lower the inhibition of manganese peroxidase. The inhibition is 50 times less when the enzymes are embedded in gold-coated nanoparticle clusters. The nanoparticles have no intrinsic catalytic activities in this range of concentration of hydrogen peroxide (0.001 to 10 mM).

FIG. 6 is a graph showing the effect of $H_2O_2$ on DMP oxidation velocity catalyzed by versatile peroxidase at 2.5 nM, Au-M60 at different concentrations, and BNCs thereof at pH 3.5 in malonate buffer (50 mM). The x-axis is on a $log_{10}$ scale for convenience. The BNCs (gold coated nanoparticles) increase the activity and lower the inhibition of versatile peroxidase. The inhibition is 28 times less when the enzymes are embedded in gold-coated nanoparticles. The nanoparticles have no intrinsic catalytic activities in this range of concentration of hydrogen peroxide (0.001 to 10 mM).

As shown in FIGS. 5 and 6, with increasing concentrations of Au-MNPs, the peak velocities decreased but the optimal concentration of $H_2O_2$ was shifted toward higher concentrations. This was reflected in the kinetic parameters as the $V_{max}$ decreased with increasing concentration of MNPs. The inhibition constant (K) of the enzyme increased with increasing concentration of Au-MNPs. Compared to free manganese peroxidase, the inhibition decreased by 50 fold with Au-M90, and about 30 times with Au-M60. Remarkably, it is believed to be the lower $K_m$ and the higher $K_i$ values that drove the relative increase in velocity observed for BNCs. The coating with gold prevents the dissolution of the magnetic core (magnetite) in the buffer necessary for enzymes activities. Without gold-coating, magnetite nanoparticles are typically fully dissolved in 10 minutes below pH 5 in malonic acid. The BNCs (gold coated nanoparticles) increase the activity and lower the inhibition of manganese peroxidase.

The peroxidase-based catalytic system was applied to the depolymerization of grass biomass, with the production of soluble aromatics followed by UV and fluorescent spectroscopy. For this application, the manganese peroxidase and versatile peroxidase were combined in equimolar ratio. Initial tests using hydrogen peroxide directly were not conclusive for the amount of enzyme used. The concentration of peroxide needed to detect any activity of biomass would be inhibitory if added at once. Enzyme stability can be notably improved by maintaining a lower oxidant concentration over the course of the reaction. In this case, background oxidations are reduced by keeping the hydrogen peroxide concentration to low levels by carefully controlling the inputs of peroxide. This effect of excess of hydrogen peroxide "shutting down" enzymes is well known and has been classically addressed by complex reactor designs to precisely control the $H_2O_2$ feeding streams with feedback loops. To circumvent this issue, the in situ production of $H_2O_2$ was chosen by coupling peroxidase enzymes with a peroxide producing enzyme such as the well-known glucose oxidase (Gox). Gox converts glucose to hydrogen peroxide and gluconolactone in the presence of oxygen.

Figure 7A:
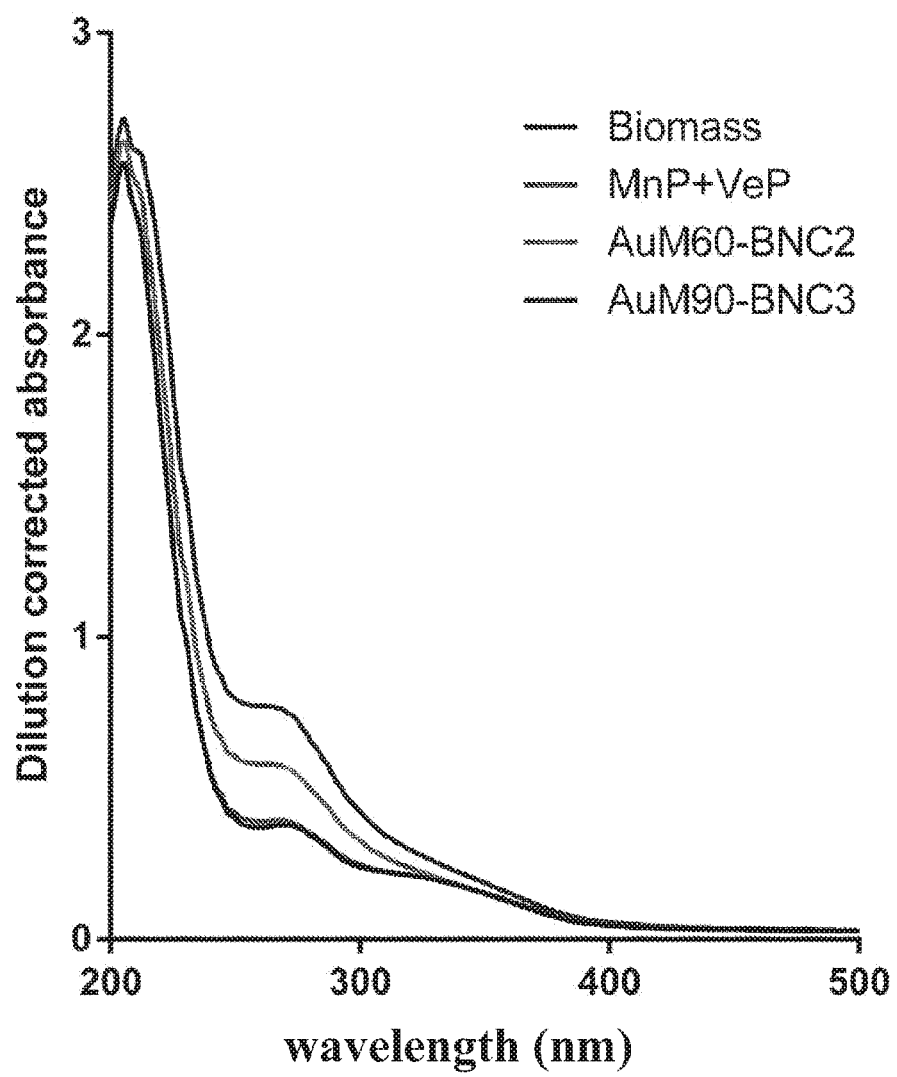
FIG. 7A shows dilution corrected spectra characteristic to water soluble lignin monomers and oligomers.
Figure 7B:
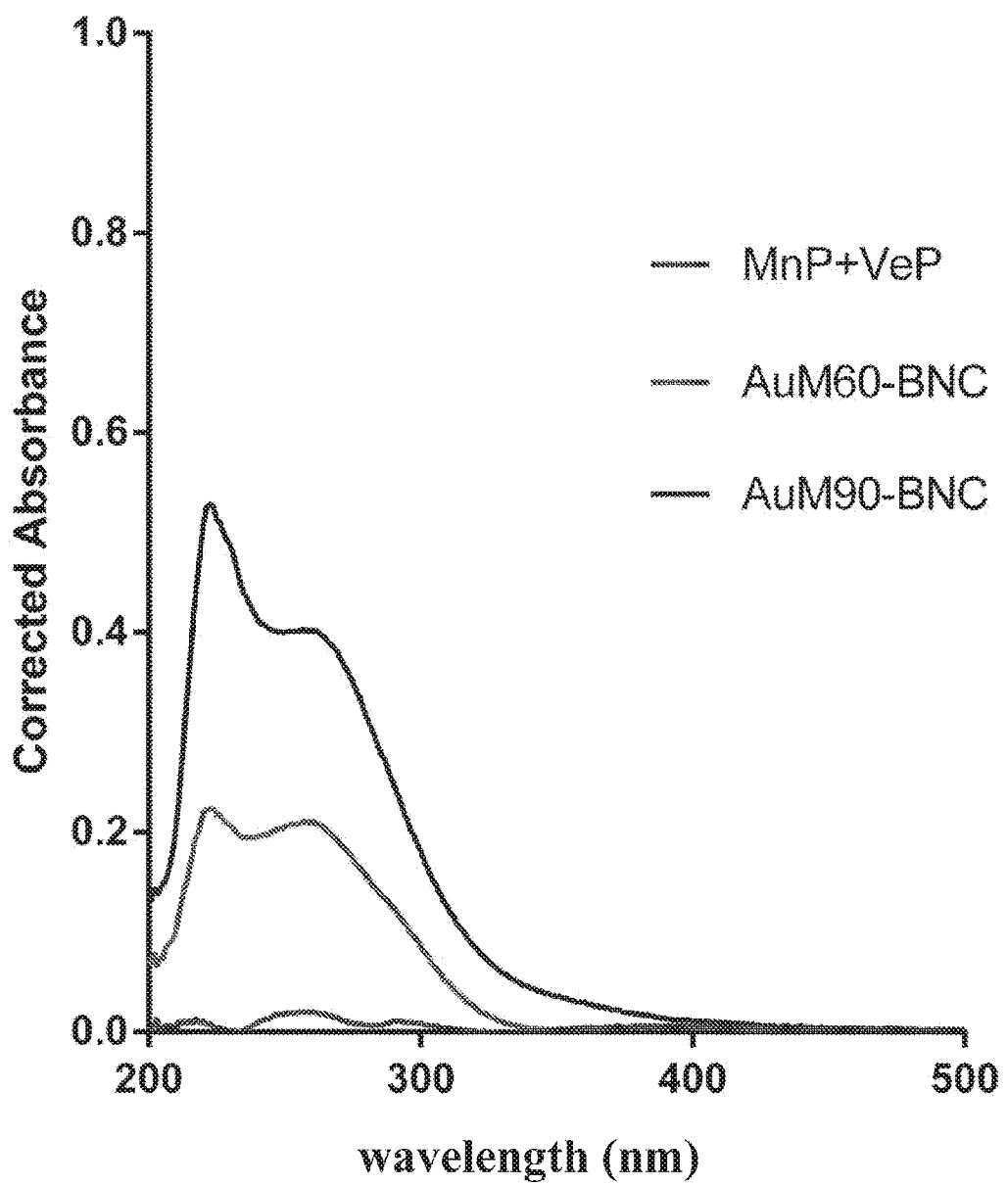
FIG. 7B shows biomass control corrected spectra. BNCs were formed with 25 mM of MnP and VeP (50 mM total enzyme) and 400 µg·ml$^{-1}$ of Au-MNPs. The reaction was initiated with 0.2 mM of $H_2O_2$ and incubated for 24 hours. The BNCs increase the release of aromatics from biomass.
Figure 8A:
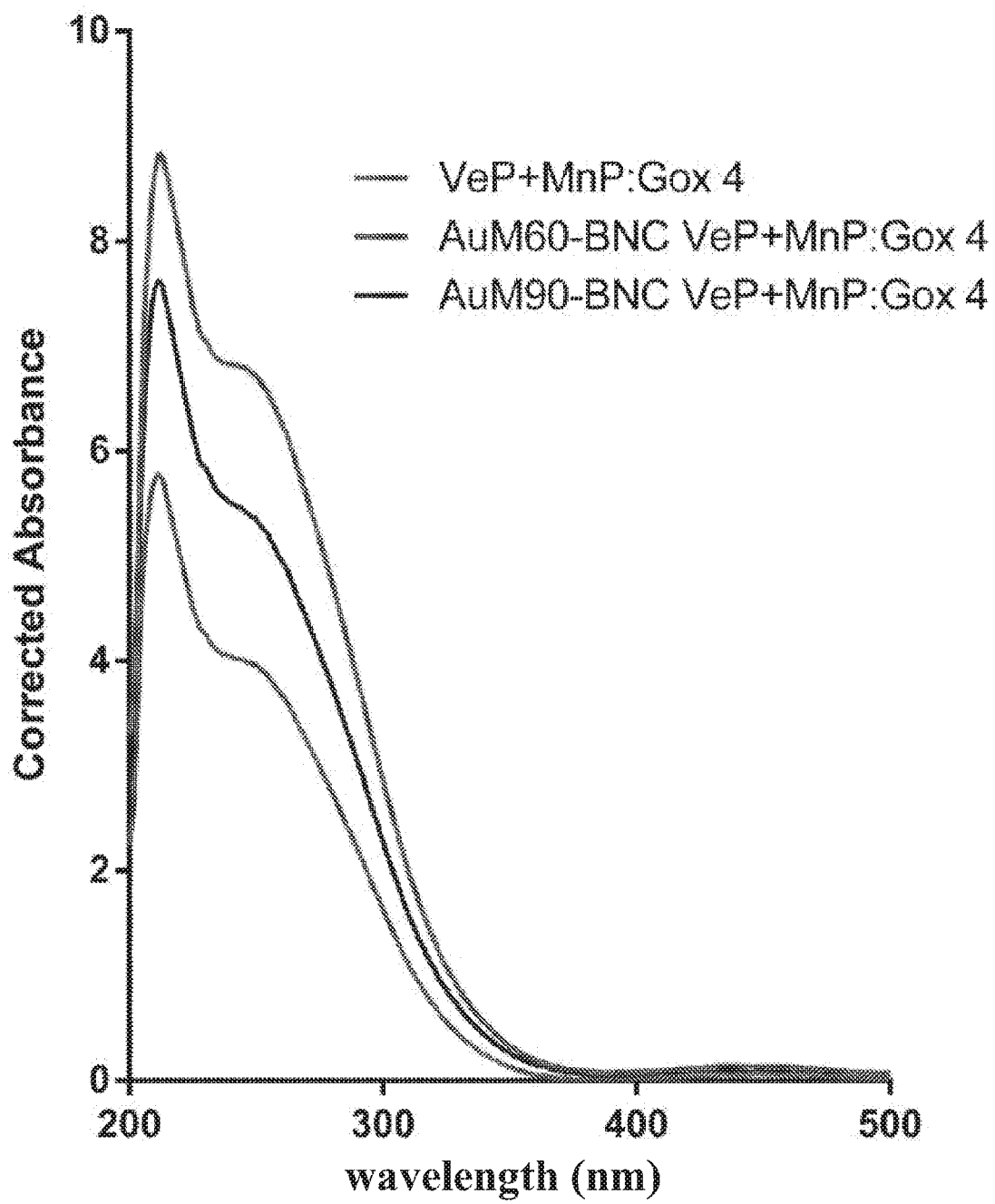
FIGS. 8A-8C. Spectra showing use of manganese peroxidase and versatile peroxidase in the presence of glucose oxidase for lignin depolymerization of biomass feedstock (mixed grasses). The glucose oxidase produces hydrogen peroxide in the presence of glucose. Corrected spectra of biomass hydrolysates at 12 hours for different peroxidase-to-oxidase molar ratio. BNCs were formed with manganese peroxidase and versatile peroxidase at 25 nM each—15 µg·ml$^{-1}$ Au-MNPs).
Figure 8B:
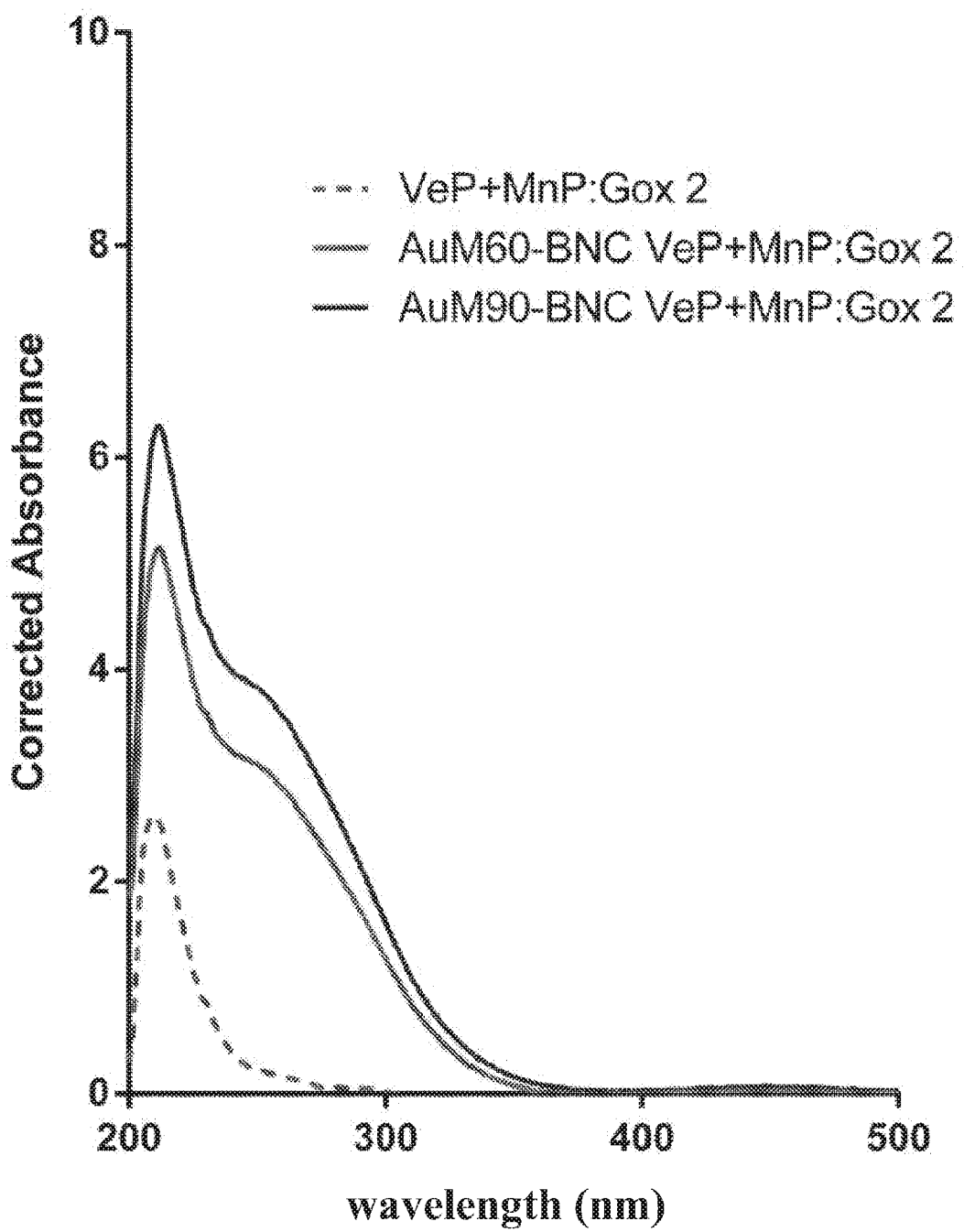
Figure 8C:
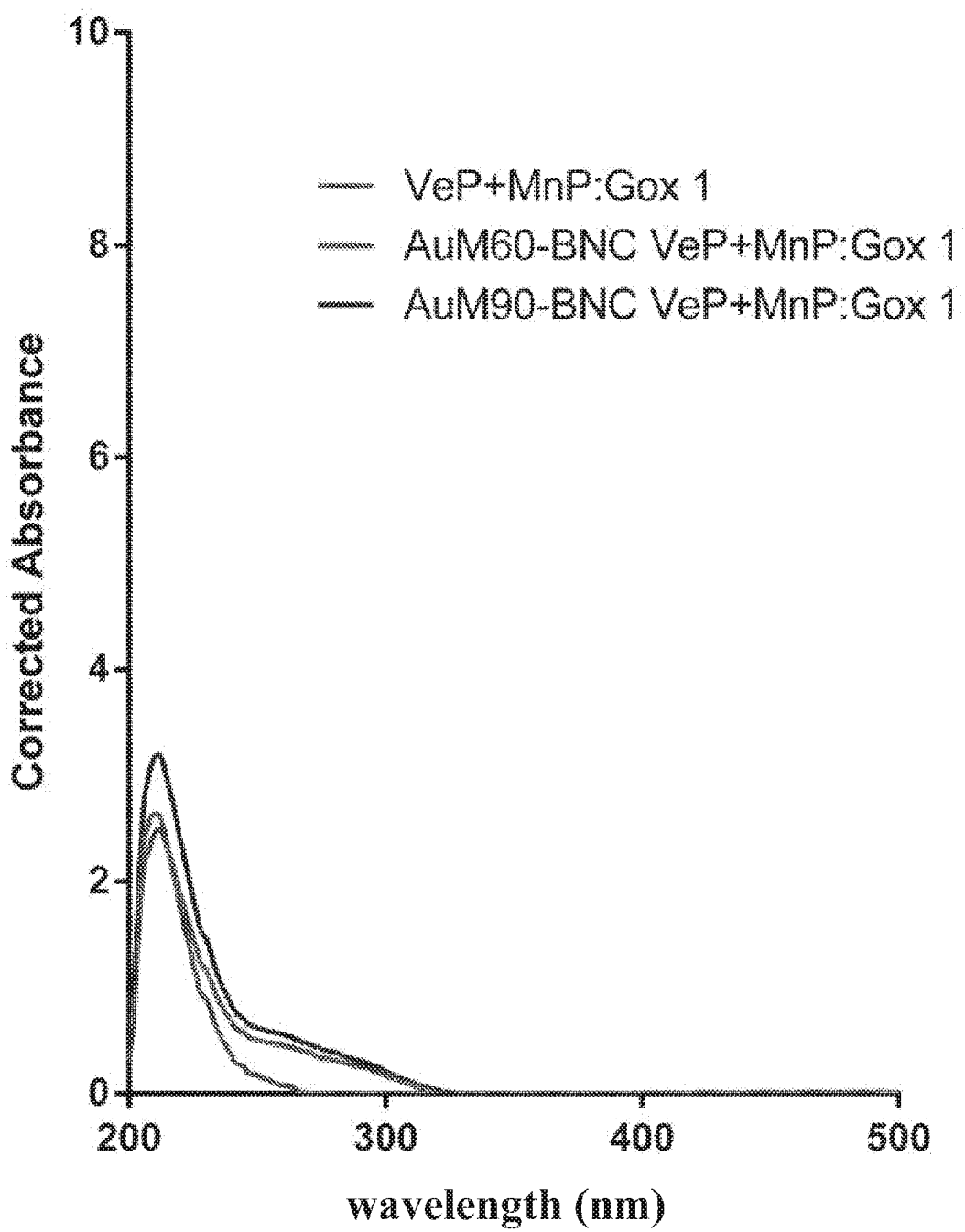

The glucose oxidase-peroxidase system was combined to assemble with the gold-coated nanoparticles for biomass conversion. As shown in FIGS. 7A, 7B, 8A, 8B, and 8C, the hybrid systems of peroxidase+oxidase have higher activities on biomass than enzymes alone. FIG. 7A shows the UV-vis spectra of the supernatant after treatment with a mixture of manganese peroxidase and versatile peroxidase immobilized or not within gold-coated BNCs. FIG. 7B shows the same spectra when the reference biomass spectra has been subtracted. In these experimental conditions and using hydrogen peroxide as oxidant, the enzymes only have an activity on the release of aromatic compounds from biomass if they are immobilized in BNCs. Adding peroxide directly in the biomass slurries can induce a substrate inhibition of the enzymes. Hence, peroxide needs to be added incrementally in small quantities to avoid reaching inhibitory levels. To circumvent this, the in situ production of hydrogen peroxide was implemented by adding glucose oxidase (Gox) within the peroxidase BNCs (FIG. 8A, 8B, 8C). Gox converts glucose to gluconolactone and hydrogen peroxide in presence of oxygen. This oxidase/peroxidase system permits adjustment in the rate of production of hydrogen peroxide by the oxidase to meet the rate of consumption by the peroxidase. In the appropriate steady-state conditions, the hydrogen peroxide does not reach inhibitory concentration. The catalysts (BNCs) were tested on real biomass and the release of aromatics molecules (from lignin) was monitored in the UV range (spectra corrected and subtracted against control samples). By comparing FIGS. 8A, 8B and 8C, an optimal ratio of 1 molecule of Gox for 4 molecules of peroxidase enzymes was found to be more appropriate. The activity of the BNCs embedding manganese peroxidase, versatile peroxidase, and glucose oxidase was found to be about 30% higher on real biomass compared to the free enzymes system. On real biomass, as shown in FIGS. 8B and 8C, the Au-MNPs protect against inhibition when the concentration of peroxide is more detrimental to the free enzymes.

The BNCs increase the release of soluble aromatics from biomass when manganese peroxidase and versatile peroxidase are used in combination and in presence of manganese. The BNCs made with gold-coated magnetic nanoparticles can be immobilized on magnetic scaffolds for ease of reusability. The rate of production of hydrogen peroxide can be controlled by modifying the concentration of glucose oxidase in BNCs. However, gold coated nanoparticles with more gold (e.g., AuM90) provide higher rates of conversion due to lower inhibition of the enzyme from higher concentration of hydrogen peroxide.

Phenol Removal

Figure 9:
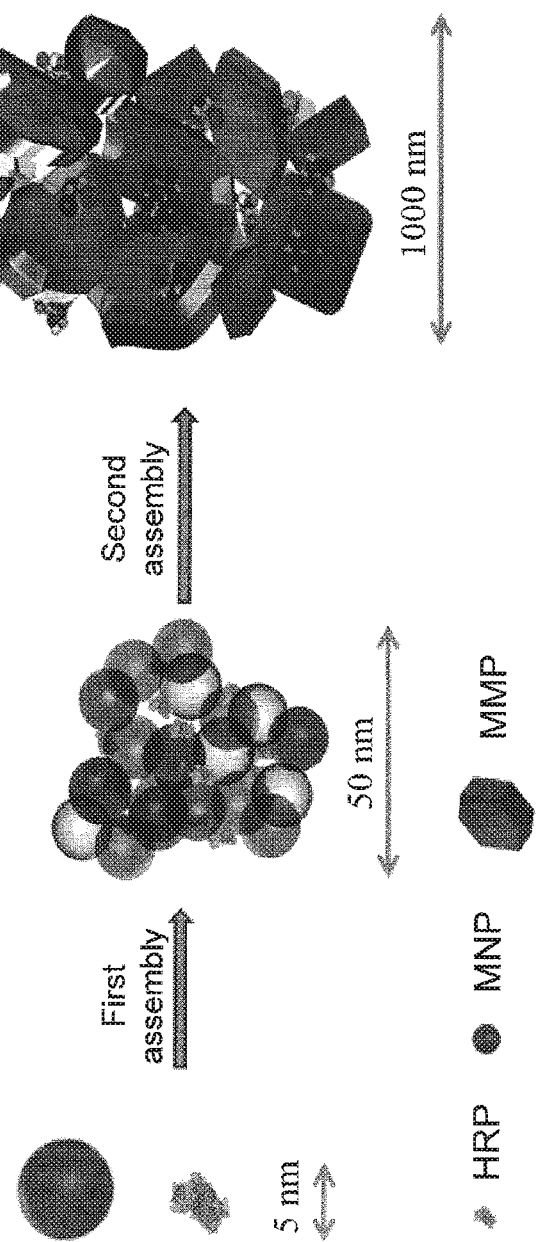
FIG. 9. Schematic showing the assembly of BNCs of horseradish peroxidase templates on magnetite microparticles to form hierarchical macroporous catalysts for applications including phenol remediation and chemical conversion of aromatics.

In this example is reported a new family of hierarchical hybrid catalysts containing horseradish peroxidase (HRP) assembled with magnetic nanoparticles and their incorporation into microparticles, and their use in advanced oxidation processes and removal of phenol. The hierarchical hybrid catalysts can be assembled by the process shown in FIG. 9. The hybrid peroxidase catalysts exhibit activity three times higher than free HRP and are able to remove three times more phenol compared to free HRP under similar conditions. Phenol in this case is a model molecule representative of phenolic compounds; the efficacy of BNCs towards phenol removal was evaluated.

Figure 10:
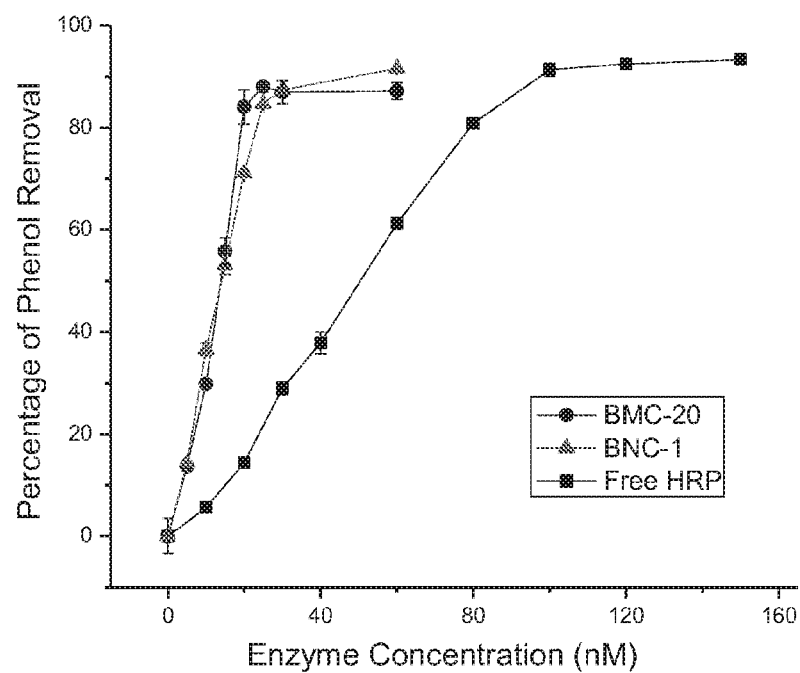
FIG. 10. Graph showing extent of phenol removal using BNC and BMC after 12 hours at room temperature at equimolar concentration of phenol and $H_2O_2$ (1 mM). The error bars are the standard deviation of triplicates. The templating of the BNCs onto microparticles to form mesoporous catalysts is not detrimental to the activity of the BNCs.

As shown in FIG. 10, the templating of the BNCs onto magnetic scaffolds does not change the activities of the BNCs trapped enzymes that are more efficient than free enzymes. The results show that all systems actively remove phenol but the BNCs are more effective than the free enzyme for the same concentration of HRP. Moreover, to reach more than 90% phenol removal, the amount of HRP required in the BNCs is three to four times less than that required for free HRP.

Figure 11A:
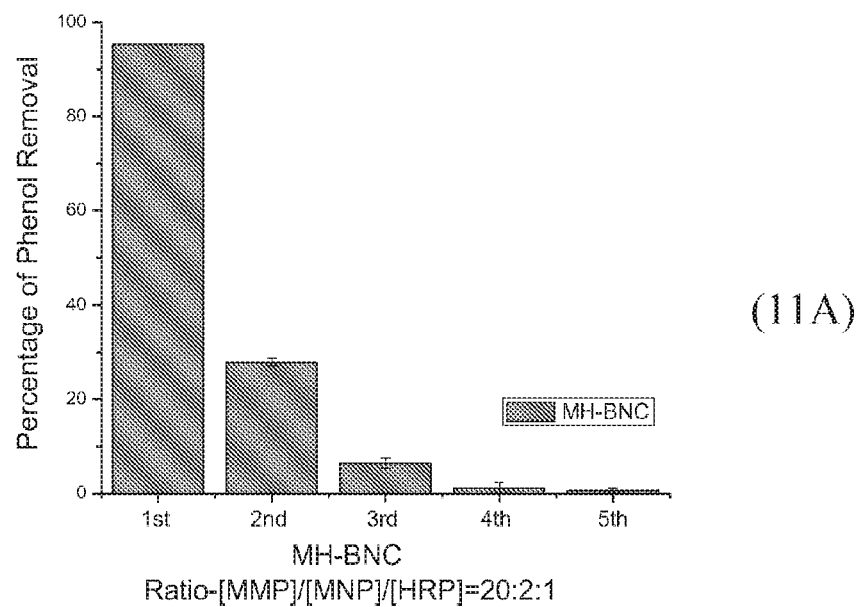
FIGS. 11A, 11B. Bar charts showing reuse performance of catalysts after each cycle for five cycles for phenol removal: [phenol]=[$H_2O_2$]=1 mM; reaction time 2 hours at room temperature; [HRP]=30 nM, [MNP]=60 ug/ml.
Figure 11B:
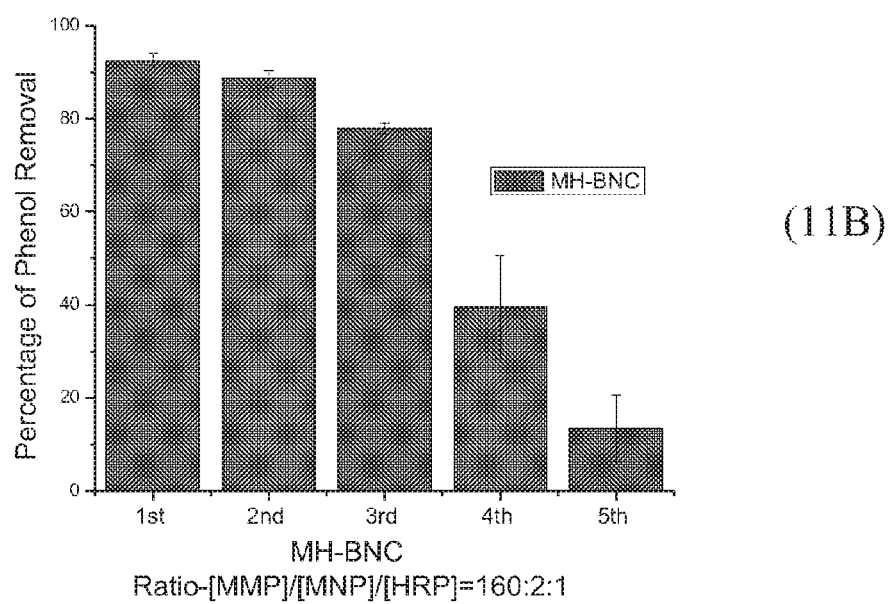
Figure 12A:
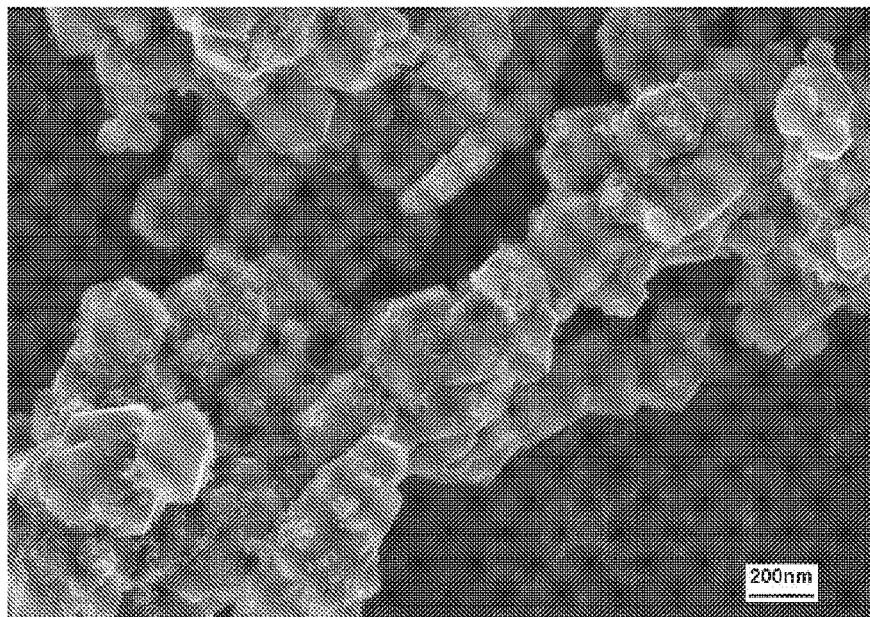
FIG. 12A, 12B. Scanning electronic microscope (SEM) images of the horseradish peroxidase BNCs templated on magnetite microparticles and two different ratios of BNCs. The assemblies of BNCs onto the surface of microparticles is a self-assembling process driven by magnetic interactions.
Figure 12B:
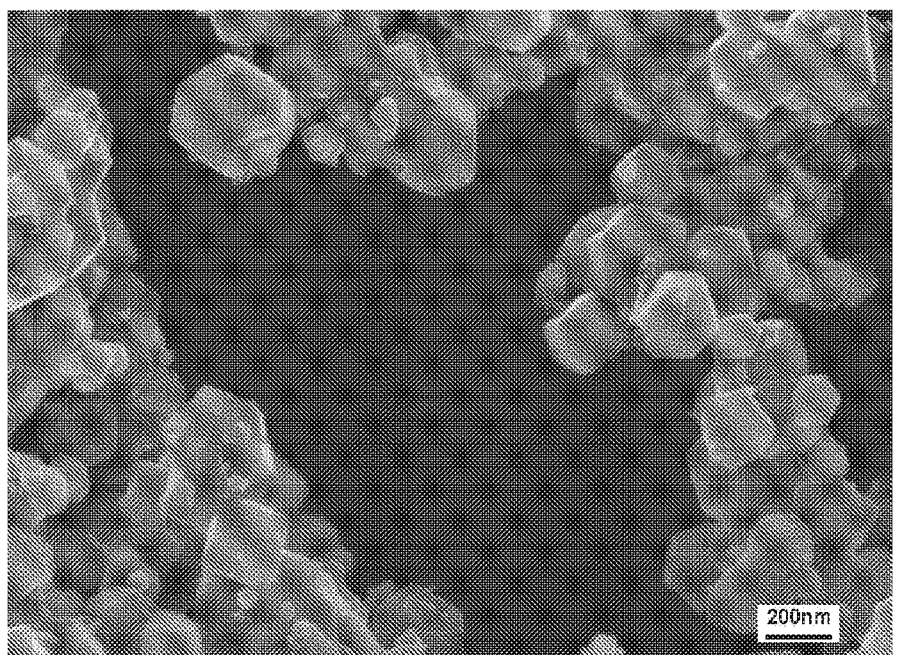

The assembly of BNCs onto magnetic scaffold can be controlled by the ratio of magnetic microparticles to BNCs as shown in the micrographs in FIGS. 12A and 12B. In FIG. 12A, there is an excess of BNCs that can be seen on the surface of the sample holder surface. In FIG. 12B, additional magnetic scaffold was added to capture the excess BNCs, which results in an absence of free BNCs. The foregoing results demonstrate the process of templating the BNCs onto magnetic scaffolds to create hierarchical structures. At least one advantage of such structures is illustrated in the phenol removal results shown in FIGS. 11A and 11B. Compared to FIG. 11A, templated BNCs (FIG. 11B) can be easily removed and retain activity for several reaction cycles in batch conditions. While the activity of the free enzyme drops quickly after the first cycle, the templated BNCs retain significant activity after the fifth cycle in these batch conditions compared to the free enzymes.

Figure 13:
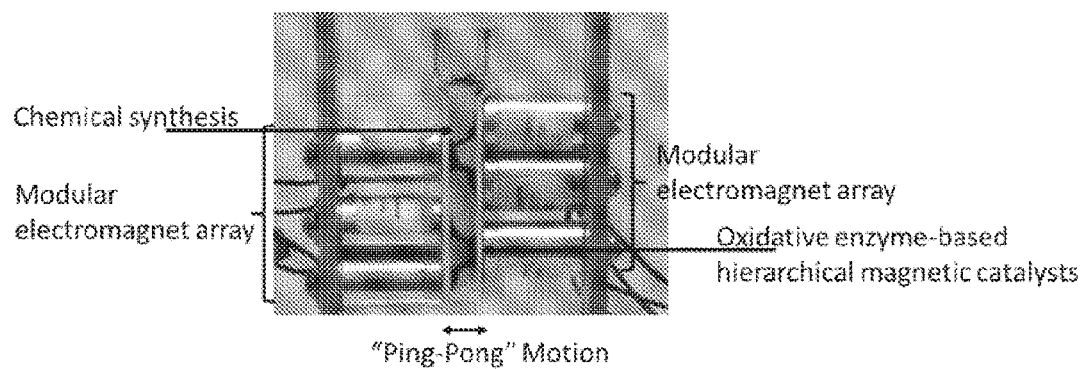
FIG. 13. Photograph showing a V-shape conformation of the magnetic reactors; the electromagnets are paired and cycled on a 1-2 basis. The prototype system has been designed with electromagnets (tubular 9.6×16.7 mm, Series E-66-38, Magnetic Sensor Systems, CA), a simple microcontroller and interface circuits between the microcontroller and electromagnets. The electromagnets are mounted on a custom stand, which allows them to be positioned in various configurations at the side of a small bioreactor consisting of disposable UV transparent plastic micro-cuvettes with a 0.5 cm cross-section.
Figure 14:
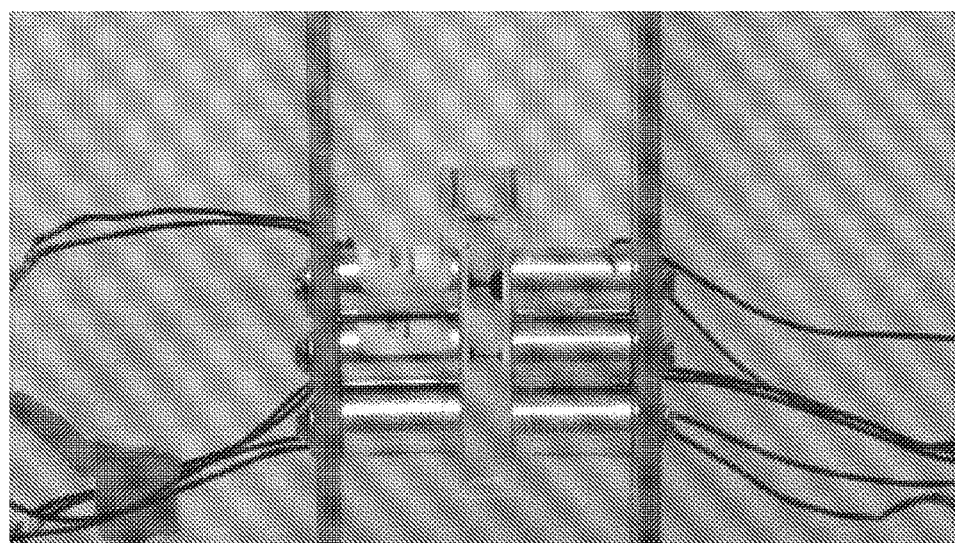
FIG. 14. Photograph showing an I-shape conformation of the magnetic reactors; the electromagnets are paired and cycled on a 1-1 basis. The pink color is characteristic of the synthesis of quinoneimine from phenol and aminopyrene using high-efficiency horseradish peroxidase-based magnetic catalysts. This reaction illustrates the removal of phenols and the synthesis chemistry of pigments, dyes, aromas and fine chemicals.

In general, HRP catalyzes the oxidation of phenolic compounds in the presence of $H_2O_2$, thereby producing free radicals. The phenoxy radicals subsequently react with each other in a non-enzymatic process to condense or to form polymers. To use the hierarchical catalysts in a continuous flow fashion, a reactor system composed of electromagnets was herein designed. This system is illustrated in FIG. 13 and FIG. 14. These figures depict, respectively, a V-shape configuration and an I-shape configuration. The back-and-forth motion of the catalysts driven by the electromagnets maintains the catalysts in a given reaction zone of the reactors. The motion of the catalysts is driven by the geometry of the electromagnet arrays, sequence of on/off powering of the electromagnets, and intensity of the magnetic field generated by the electromagnets. Applied to remediation of phenols and aromatics, the configuration permits segregating reaction zones inside the volume of the reactors.

Figure 15:
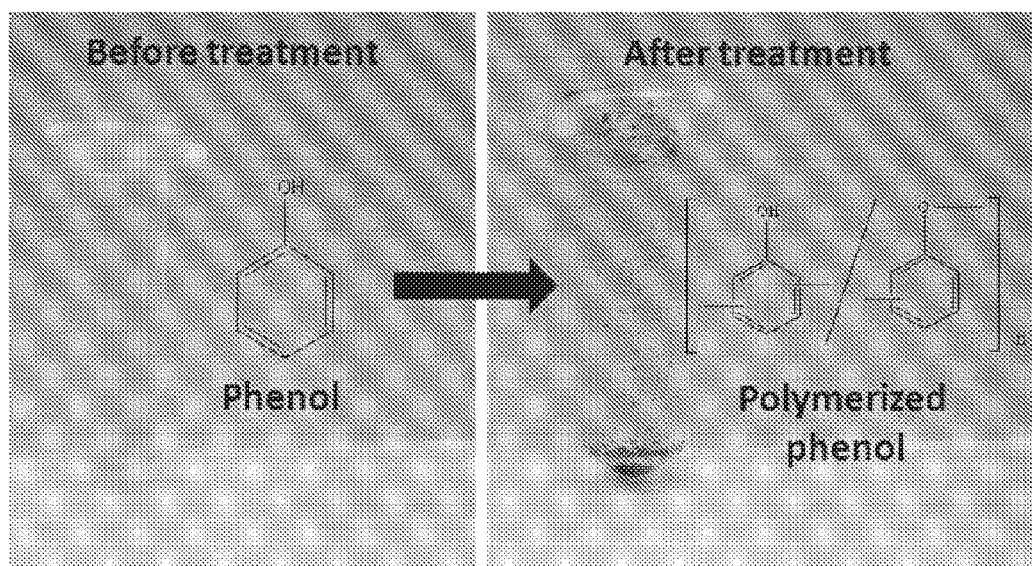
FIG. 15. Schematic showing the use of BNCs for phenol removal by oxidative polymerization. The phenol molecules are oxidized to phenoxy-radicals that polymerize with each other. The reaction is characteristic of the remediation of aromatics and the polymerization by oxidative coupling.
Figure 17:
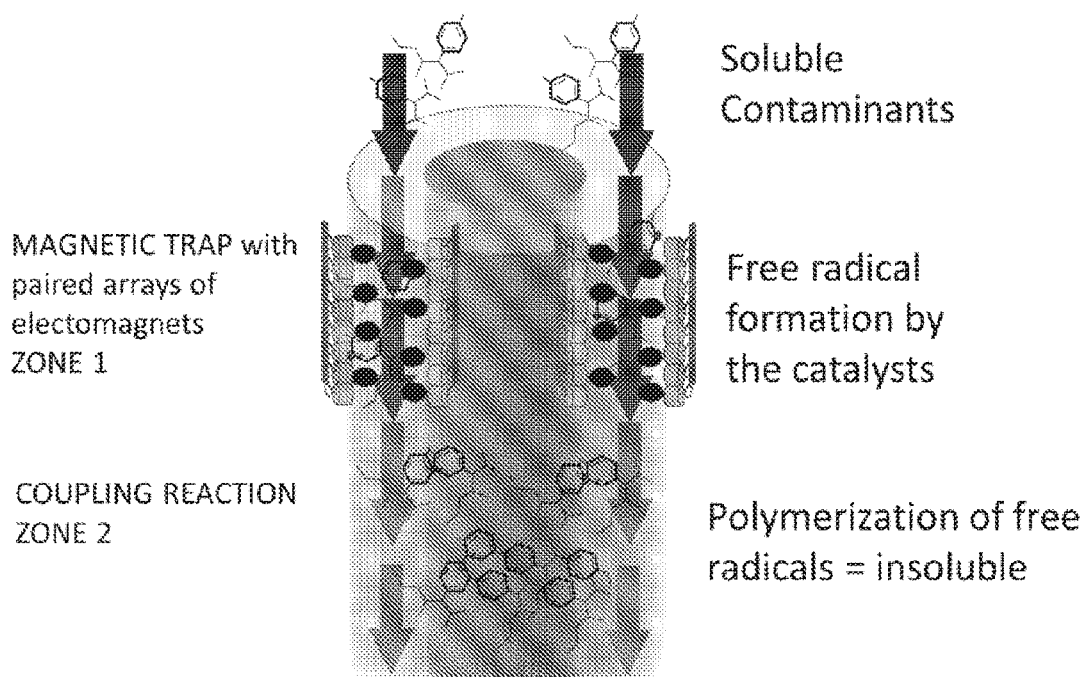
FIG. 17. Schematic showing the core of the magnetic reactors for the decoupling of free radical generation and polymerization.

In the case of phenol, using a suitable electromagnet configuration, such as described above, the production of the free radicals can be separated from the polymerization of the polyphenols, as schematized in FIG. 17. The enzymes (and enzyme trapped within BNCs) oxidize the phenol to its free radical form. These highly reactive radicals react with each other to form polyphenols. These polyphenols can be further condensed by inclusion of a coagulating agent or divalent salt. The phenol removal (polymerization) process described above is generically illustrated in FIG. 15. The brown particles shown in the right portion of the scheme are polyphenols resulting from the polymerization by the BNCs. These micrometric to millimetric size particles of polyphenols can be easily removed by sedimentation or filtration.

Figure 16:
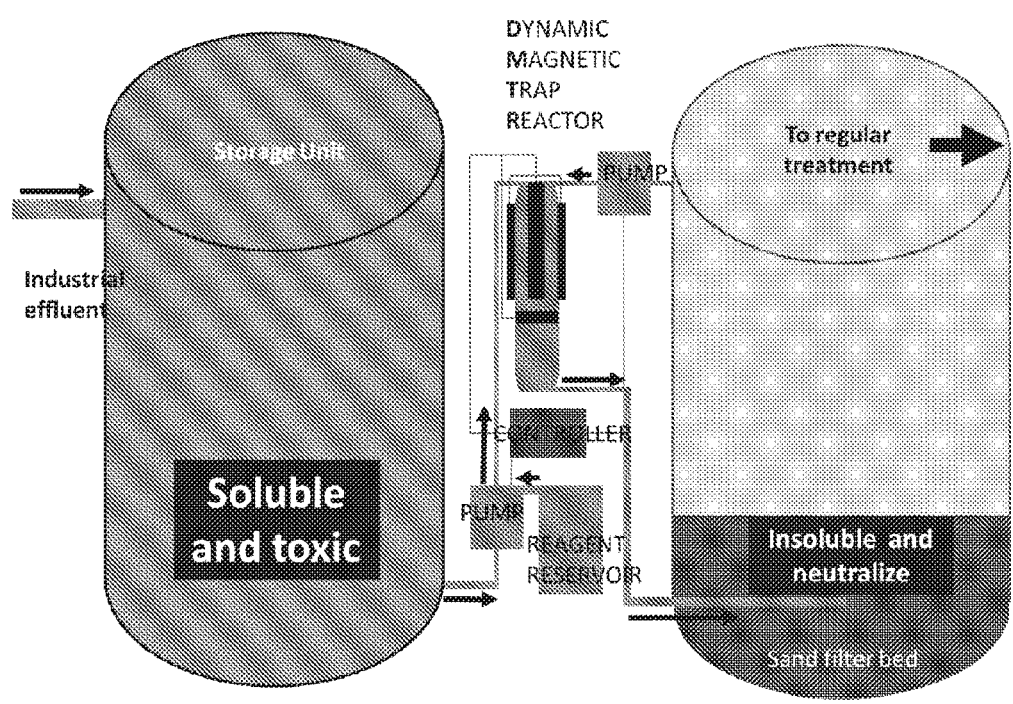
FIG. 16. Schematic showing the integration of magnetic reactors for water treatment.

An example of integration of such reactors for water remediation applications is illustrated in FIG. 16. The magnetic reactor maintains the enzyme-based catalysts against the flow of water and is placed between the reservoir of contaminated fluid and the receiving reservoir. The polymerized contaminants are separated from the water by being passed through a particulate bed, such as sand or other particulate materials. The water can be cycled several times in the system according to the severity of the contamination.

The hybrid catalysts, as described above, reduce substrate inhibition and limit inactivation from reaction products, which are common with free or conventionally immobilized enzymes. Reusability is improved when the HRP/magnetic nanoparticle hybrids are supported on micron-sized magnetic particles, and can be confined with the specially designed magnetically-driven reactors described above. The reported performance of the hybrid catalyst makes them attractive for several industrial and environmental applications and pave the way for practical applications by eliminating most of the limitations that have prevented the use of free or conventionally immobilized enzymes.

While there have been shown and described what are at present considered the preferred embodiments of the invention, those skilled in the art may make various changes and modifications which remain within the scope of the invention defined by the appended claims.

What is claimed is:

1. A method for halogenation reactions of phenols, the method comprising reacting a phenol with a hierarchical catalyst composition comprising a continuous macroporous scaffold in which is incorporated self-assembled mesoporous aggregates of magnetic nanoparticles containing a halogenating enzyme embedded in mesopores of said mesoporous aggregates of magnetic nanoparticles, to produce a halogenated phenol.

2. The method of claim 1, wherein said halogenating enzyme is a chloroperoxidase.

3. The method of claim 1, further comprising magnetic particles, not belonging to said mesoporous aggregates of magnetic nanoparticles, embedded in said continuous macroporous scaffold.

4. The method of claim 1, wherein said continuous macroporous scaffold has a polymeric composition.

5. The method of claim 1, wherein said continuous macroporous scaffold has macropores having a pore size greater than 50 nm.

6. The method of claim 1, wherein said continuous macroporous scaffold has macropores having a pore size of at least 200 nm.

7. The method of claim 1, wherein said continuous macroporous scaffold has macropores having a pore size up to 100 μm.

8. The method of claim 1, wherein said mesopores have a size of at least 1 nm and up to 50 nm.

* * * * *